(12) United States Patent
Nakata et al.

(10) Patent No.: US 10,297,766 B2
(45) Date of Patent: May 21, 2019

(54) COMPOSITION CONTAINING NAPHTHALOCYANINE DERIVATIVE, PHOTOELECTRIC CONVERSION ELEMENT CONTAINING THE SAME, AND IMAGING DEVICE

(71) Applicant: Panasonic Intellectual Property Management Co., Ltd., Osaka (JP)

(72) Inventors: Manabu Nakata, Osaka (JP); Yuko Kishimoto, Osaka (JP); Masaya Hirade, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 15/959,097

(22) Filed: Apr. 20, 2018

(65) Prior Publication Data

US 2018/0315934 A1 Nov. 1, 2018

(30) Foreign Application Priority Data

Apr. 28, 2017 (JP) .................................. 2017-090808

(51) Int. Cl.
*H01L 51/00* (2006.01)
*H01L 31/0224* (2006.01)
(Continued)

(52) U.S. Cl.
CPC ........ *H01L 51/0078* (2013.01); *C07F 7/2224* (2013.01); *H01L 31/022408* (2013.01);
(Continued)

(58) Field of Classification Search
None
See application file for complete search history.

(56) References Cited

U.S. PATENT DOCUMENTS 8,168,781 B2 * 5/2012 Kitamura ................ C09B 47/00
106/31.46
2009/0054641 A1 2/2009 Kitamura et al.
(Continued)

FOREIGN PATENT DOCUMENTS

JP 63-005093 1/1988
JP 2003-234460 8/2003
(Continued)

OTHER PUBLICATIONS

The Extended European Search Report dated Jun. 14, 2018 for the related European Patent Application No. 18167982.0.
(Continued)

*Primary Examiner* — Jack S Chen
(74) *Attorney, Agent, or Firm* — McDermott Will & Emery LLP

(57) ABSTRACT

A composition contains a compound represented by the following formula:
(Continued)

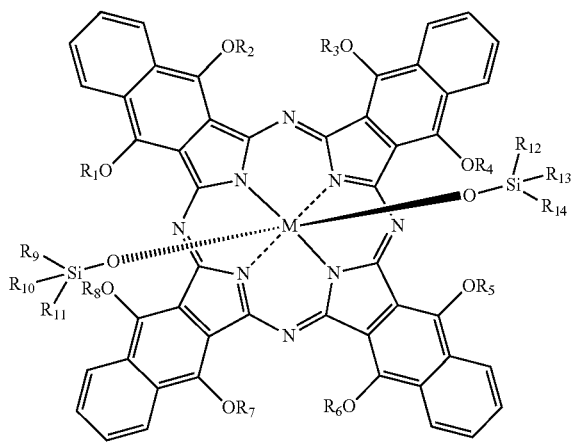

where M represents either of Si and Sn, $R_1$ to $R_8$ each independently represent an alkyl group containing three or less carbon atoms, and $R_9$ to $R_{14}$ each independently represent an alkyl group.

9 Claims, 8 Drawing Sheets

(51) Int. Cl.
    *C07F 7/22*         (2006.01)
    *H01L 51/42*       (2006.01)
(52) U.S. Cl.
    CPC ............. *H01L 31/022475* (2013.01); *H01L 51/0077* (2013.01); *H01L 51/0094* (2013.01); *H01L 51/42* (2013.01)

(56) References Cited

U.S. PATENT DOCUMENTS

| | | |
|---|---|---|
| 2009/0224235 A1 | 9/2009 | Kitamura et al. |
| 2012/0204960 A1 | 8/2012 | Kato et al. |
| 2018/0315934 A1* | 11/2018 | Nakata .................. C07F 7/2224 |

FOREIGN PATENT DOCUMENTS

| | | |
|---|---|---|
| JP | 2009-054606 | 3/2009 |
| JP | 2009-212389 | 9/2009 |
| JP | 2010-232410 | 10/2010 |
| JP | 2011-119694 | 6/2011 |
| JP | 2016-225456 | 12/2016 |
| WO | 2013/102985 | 7/2013 |

OTHER PUBLICATIONS

Aoudia M et al: "Synthesis of a Series of Octabutoxy- and Octabutoxybenzophthalocyanines and Photophysical Properties of Two Members of the Series", Journal of the American Chemical Society, American Chemical Society, US, vol. 119, No. 26, Jan. 1, 1997 (Jan. 1, 1997), pp. 6029-6039, XP002186613.

Ryo Hirohashi et al., "Phthalocyanines as Functional Dyes", IPC (2004), Jul. 20, 2004, pp. 29-77(Partial Translation).

Hirohusa Shirai et al., "Phthalocyanines—Chemistry and Function-", IPC (1997), Feb. 28, 1997, pp. 1-62(Partial Translation).

Serap Gunes et al., "Conjugated Polymer-Based Organic Solar Cells", Chemical Reviews, American Chemical Society, vol. 107, No. 4 (2007), Apr. 11, 2007, pp. 1324-1338.

Jana Zaumseil et al., "Electron and Ambipolar Transport in Organic Field-Effect Transistors", Chemical Reviews, American Chemical Society, vol. 107, No. 4 (2007), Mar. 23, 2007, pp. 1296-1323.

Cheolbeom Bae et al., "Synthesis and characterization of near-infrared absorption tin octabutoxy naphthalocyanines", Elsevier, Polyhedron 26 (2007), Feb. 7, 2007, pp. 2810-2816.

* cited by examiner

COMPOSITION CONTAINING NAPHTHALOCYANINE DERIVATIVE, PHOTOELECTRIC CONVERSION ELEMENT CONTAINING THE SAME, AND IMAGING DEVICE

BACKGROUND

1. Technical Field

The present disclosure relates to a composition containing a naphthalocyanine derivative, a photoelectric conversion element, and an imaging device.

2. Description of the Related Art

For conventional naphthalocyanine derivatives, an example of a molecular structure in which trialkylsiloxy groups serving as ligands connecting a central metal are bonded is reported in Japanese Unexamined Patent Application Publication No. 63-5093. Furthermore, an example of a molecular structure in which a butoxy group, which contains four carbon atoms, bonded to an oxygen atom bonded to an α-carbon atom of a naphthalene ring of a naphthalocyanine skeleton is reported in Cheolbeom Bae et al., "Synthesis and characterization of near-infrared absorption tin octabutoxy naphthalocyanines", Polyhedron, Elsevier, vol. 26, no. 12 (2007), pp. 2810-2816.

SUMMARY

In one general aspect, the techniques disclosed here feature a composition containing a compound represented by the following formula:

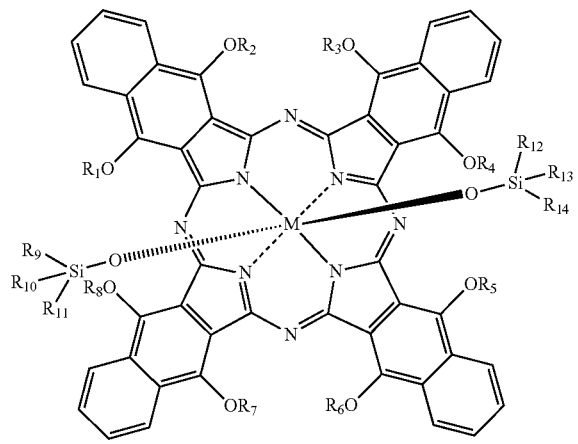

where M represents either of Si and Sn, $R_1$ to $R_8$ each independently represent an alkyl group containing three or less carbon atoms, and $R_9$ to $R_{14}$ each independently represent an alkyl group.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1A:
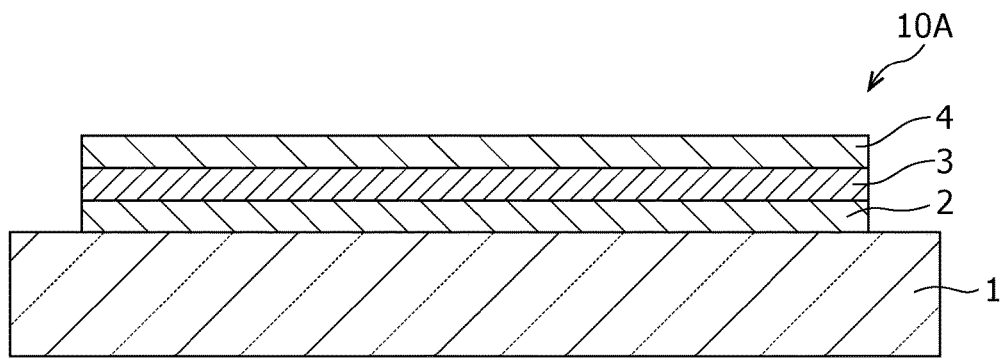
FIG. 1A is a schematic sectional view of an example of a photoelectric conversion element according to an embodiment of the present disclosure.

Underlying Knowledge Forming Basis of the Present Disclosure

Hitherto, a naphthalocyanine derivative with a molecular structure in which the number of carbon atoms in a substituent introduced into an α-chain of a naphthalene ring of a naphthalocyanine skeleton is greater than 4 has been used to ensure high solubility in solvents because naphthalocyanine derivatives have extremely low solubility in organic solvents. It is conceivable that the formation a film from a naphthalocyanine derivative having a substituent containing three or less carbon atoms and the synthesis of the naphthalocyanine derivative are difficult.

The inventors have found that a naphthalocyanine derivative, serving as a compound with light absorption characteristics, having a substituent containing three or less carbon atoms has high solubility in solvents and can be synthesized.

The present disclosure provides a composition which has light absorption characteristics in the near-infrared region and which exhibits high photoelectric conversion efficiency in the case where the composition is formed into an element, a photoelectric conversion element, and an imaging device.

A composition according to an aspect of the present disclosure contains a compound represented by the following formula:

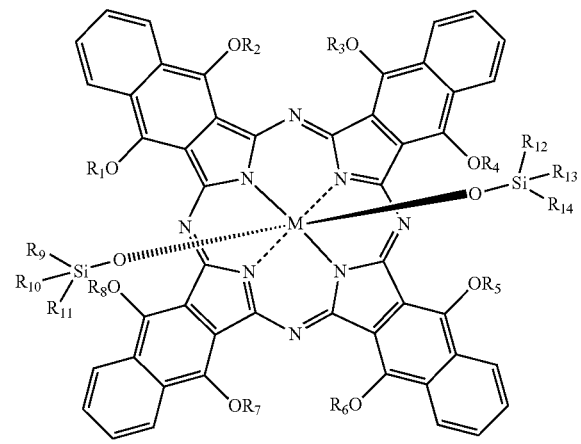

where M represents either of Si and Sn, $R_1$ to $R_8$ each independently represent an alkyl group containing three or less carbon atoms, and $R_9$ to $R_{14}$ each independently represent an alkyl group.

This allows the composition to have high light absorption characteristics in the near-infrared region and enables the dark current in a photoelectric conversion element to be reduced because the composition contains the compound represented by the above formula. Therefore, a photoelectric conversion element and imaging device exhibiting high photoelectric conversion efficiency can be obtained using the composition.

In the above formula, M may be, for example, Sn.

This enables the compound represented by the above formula to be readily synthesized.

In the above formula, $R_1$ to $R_8$ may be, for example, ethyl groups.

This enables high photoelectric conversion efficiency to be exhibited.

In the above formula, $R_9$ to $R_{14}$ may each independently represent, for example, an alkyl group containing 10 or less carbon atoms.

This enables the compound represented by the above formula to be readily synthesized.

In the above formula, $R_9$ to $R_{14}$ may be, for example, hexyl groups.

This enables the compound represented by the above formula to be readily synthesized.

A photoelectric conversion element according to an aspect of the present disclosure includes a photoelectric conversion film containing the above composition. The photoelectric conversion element may include a first electrode, a second electrode, and a photoelectric conversion film which is disposed between the first electrode and the second electrode and which contains the compound represented by the above formula.

The photoelectric conversion film may have, for example, a peak of absorption wavelength in the near-infrared region. The position of the peak of the absorption wavelength may be 900 nm or more.

In a photoelectric conversion element according to an aspect of the present disclosure, this allows the photoelectric conversion film to have high light absorption characteristics in the near-infrared region and enables the dark current to be reduced. Therefore, the photoelectric conversion element can exhibit high photoelectric conversion efficiency in a wide range of the near-infrared region.

An imaging device according to an aspect of the present disclosure includes a substrate and a unit pixel cell. The unit pixel cell includes a charge detection circuit provided in the substrate, a photoelectric converter disposed on the substrate, and a charge storage node electrically connected to the charge detection circuit and the photoelectric converter. The photoelectric converter includes the photoelectric conversion element.

This allows the imaging device to have high light absorption characteristics in the near-infrared region and enables the imaging device to exhibit high photoelectric conversion efficiency.

Embodiments are described below in detail with reference to the accompanying drawings.

Each of the embodiments below illustrates a general or specific example. Numerical values, shapes, materials, components, the positions of the components, ways to connect the components, steps, the order of the steps, and the like described in the embodiments below are examples and are not intended to limit the present disclosure. Among components in the embodiments below, components not described in independent claims indicating the highest concepts are described as arbitrary components. The drawings are not necessarily strict illustrations. In the drawings, substantially the same components are given the same reference numerals and will not be redundantly described or will be briefly described.

EMBODIMENTS

Embodiments of the present disclosure are described below.

Composition

A composition according to an embodiment of the present disclosure is described. The composition contains a compound represented by the following formula:

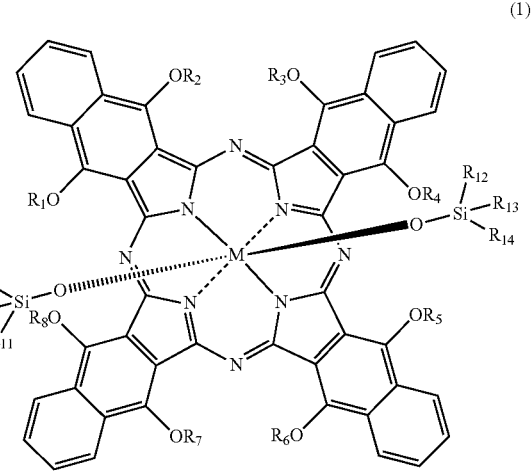

(1)

where M represents either of Si and Sn, $R_1$ to $R_8$ each independently represent an alkyl group containing three or less carbon atoms, and $R_9$ to $R_{14}$ each independently represent an alkyl group.

Since $R_1$ to $R_8$ in Formula (1) are alkyl groups containing three or less carbon atoms, the composition has a peak of absorption wavelength at a wavelength of 900 nm or more. That is, the composition has an absorption peak at a longer wavelength as compared to compounds having no alkyl groups at $R_1$ to $R_8$ and can have high light absorption characteristics over a wide range of the near-infrared region.

The compound represented by Formula (1) has an axial ligand type of structure having a central metal M and two axial ligands above and below the molecular plane; hence, the molecular interaction is reduced and vapor deposition is easy. The compound represented by Formula (1) has electron-withdrawing axial ligands; hence, the electron density of a naphthalocyanine ring is low and the highest occupied molecular orbital (HOMO) energy level and the lowest unoccupied molecular orbital (LUMO) energy level are both deep. Furthermore, the compound represented by Formula (1) has an electron-donating α-chain and therefore the LUMO level only is low. Combining these allows the reduction of the LUMO energy level to be greater than the reduction of the HOMO energy level, therefore increases the HOMO level, and reduces the energy gap (Eg). This enables near-infrared absorption and a reduction in dark current to be achieved.

In Formula (1), M is either of Si and Sn and may be Sn from the viewpoint of the easiness of synthesis.

In Formula (1), $R_1$ to $R_8$ are the alkyl groups containing three or less carbon atoms from the viewpoint of increasing the photoelectric conversion efficiency and include linear or branched alkyl groups. Examples of $R_1$ to $R_8$ include a methyl group, an ethyl group, a propyl group, and an iso-propyl group. In particular, $R_1$ to $R_8$ may be ethyl groups, which contain two carbon atoms.

$R_9$ to $R_{14}$ may be the same or different and each independently represent an alkyl group. $R_9$ to $R_{14}$ are not particularly limited and may be alkyl groups. $R_9$ to $R_{14}$ may include a linear, branched, or cyclic alkyl group or may include an unsubstituted or substituted alkyl group.

Examples of the unsubstituted alkyl group include linear alkyl groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, and an n-dodecyl group; branched alkyl groups such as an isopropyl group, an iso-butyl group, a sec-butyl group, a tert-butyl group, an iso-pentyl group, a neo-pentyl group, a tert-pentyl group, an iso-hexyl group, a sec-hexyl group, a tert-hexyl group, an iso-heptyl group, a sec-heptyl group, a tert-heptyl group, an iso-octyl group, a sec-octyl group, a tert-octyl group, an isononyl group, a sec-nonyl group, a tert-nonyl group, an iso-decyl group, a sec-decyl group, a tert-decyl group, an iso-undecyl group, a sec-undecyl group, a tert-undecyl group, an iso-dodecyl group, a sec-dodecyl group, and a tert-dodecyl group; and cyclic alkyl groups such as a cyclopropyl group, a cyclobutyl group, a cyclopentyl group, a cyclohexyl group, a cycloheptyl group, a cyclooctyl group, a cyclononyl group, a cyclodecyl group, a cycloundecyl group, and a cyclododecyl group.

The above alkyl groups may have a substituent. Examples of the substituent include an alkyl group, an alkoxy group, a halogen atom, a hydroxy group, an amino group, a thiol group, a silyl group, an ester group, an aryl group, a heteroaryl group, and other known substituents. Examples of a halogen-substituted alkyl group include a w-bromoalkyl group and a perfluoroalkyl group. Examples of a hydroxy-substituted alkyl group include a hydroxymethyl group and a hydroxybutyl group. Examples of an amino-substituted alkyl group include primary and secondary amino groups such as a dimethylamino group, a diphenylamino group, a methylphenylamino group, a methylamino group, and an ethylamino group. Examples of a thiol-substituted alkyl group include a mercapto group and an alkylthio group. Examples of a silyl-substituted alkyl group include a trimethylsilyl group, a triethylsilyl group, a tripropylsilyl group, a triisopropylsilyl group, a dimethylisopropylsilyl group, and a dimethyl-tert-butylsilyl group. Examples of an ester-substituted alkyl group include a methoxycarbonyl group, an ethoxycarbonyl group, a propoxycarbonyl group, an isopropoxycarbonyl group, a tert-butoxycarbonyl group, a phenoxycarbonyl group, an acetyloxy group, and a benzoyloxy group.

From the viewpoint of the easiness of synthesis, $R_9$ to $R_{14}$ may be alkyl groups containing 10 or less carbon atoms. From the viewpoint of solubility and the easiness of synthesis, $R_9$ to $R_{14}$ may be alkyl groups containing three or more carbon atoms. In particular, $R_9$ to $R_{14}$ may be hexyl groups, which contain six carbon atoms.

A method for synthesizing the compound represented by Formula (1) is described below.

A reaction for the formation of a naphthalocyanine ring from the compound represented by Formula (1) can be carried out in accordance with Hirofusa Shirai and Nagao Kobayashi, *Phthalocyanine—Chemistry and Function*, IPC, 1997, pp. 1-62 or Ryo Hirohashi, Keiichi Sakamoto, and Eiko Okumura, *Phthalocyanines as Functional Dyes*, IPC, 2004, pp. 29-77.

Examples of a typical method for synthesizing a naphthalocyanine derivative include a Weiler method, phthalonitrile method, lithium method, sub-phthalocyanine method, and chlorinated phthalonitrile method described in the above documents. In this embodiment, any reaction conditions may be used in a naphthalocyanine ring-forming reaction. In the naphthalocyanine ring-forming reaction, a metal, such as Sn or Si, serving as a central metal in naphthalocyanine is preferably added and a desired metal may be introduced after a naphthalocyanine derivative having no central metal is synthesized. A reaction solvent used may be any solvent and is preferably a high-boiling point solvent. In order to promote the naphthalocyanine ring-forming reaction, acid or base may be used and, in particular, base is preferably used. The optimum reaction conditions vary depending on the structure of a target naphthalocyanine derivative and may be set with reference to detailed reaction conditions described in the above documents.

Raw materials used to synthesize the above naphthalocyanine derivative may be derivatives such as naphthalic anhydride, naphthalimide, naphthalic acid, salts of naphthalic acid, naphthalic diamide, naphthalonitrile, and 1,3-diiminobenzoisoindoline. These raw materials may be synthesized by any known methods.

Photoelectric Conversion Element

A photoelectric conversion element 10A according to an embodiment of the present disclosure is described below with reference to FIGS. 1A and 1B. FIG. 1A is a schematic sectional view of an example of the photoelectric conversion element 10A.

The photoelectric conversion element 10A includes a photoelectric conversion film 3 containing the above composition. As shown in FIG. 1A, the photoelectric conversion element 10A includes a lower electrode 2 and an upper electrode 4. The photoelectric conversion film 3 is interposed between the lower electrode 2 and the upper electrode 4.

The photoelectric conversion element 10A is supported with, for example, a support substrate 1. The support substrate 1 is transparent to near-infrared light and light enters the photoelectric conversion element 10A through the support substrate 1. The support substrate 1 may be a substrate for use in general photoelectric conversion elements and may be, for example, a glass substrate, a quartz substrate, a semiconductor substrate, a plastic substrate, or the like. The expression "transparent to near-infrared light" means that something is substantially transparent to near-infrared light and the transmittance of light in the near-infrared region is, for example, 60% or more. The transmittance of light in the near-infrared region may be 80% or more and 90% or more.

Components of the photoelectric conversion element 10A are described below.

The photoelectric conversion film 3 is prepared using the composition, which contains the compound represented by Formula (1) below.

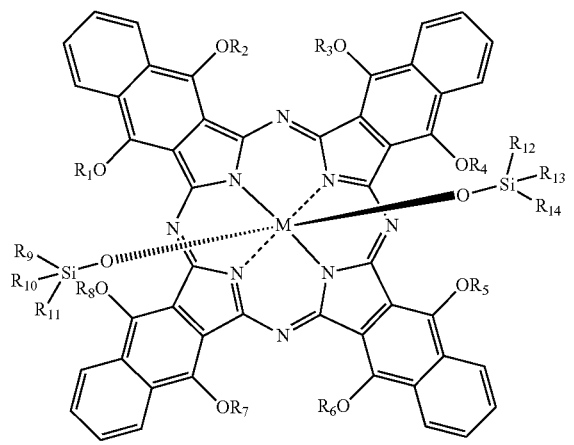

(1)

The following method can be used to prepare the photoelectric conversion film 3: for example, a coating method by spin coating, a vacuum vapor deposition method in which a film material is evaporated by heating under vacuum and is deposited on a substrate, or the like. In the case where preventing the contamination of impurities and forming multiple layers for increased functionality with a higher degree of freedom are taken into account, the vacuum vapor deposition method may be used. An evaporation system used may be a commercially available one. The temperature of an evaporation source during vapor deposition is, for example, 100° C. to 500° C. The temperature of the evaporation source during vapor deposition may be 150° C. to 400° C. The degree of vacuum during vapor deposition is, for example, $1 \times 10^{-6}$ Pa to 1 Pa. The degree of vacuum during vapor deposition may be $1 \times 10^{-6}$ Pa to $1 \times 10^{-4}$ Pa. Furthermore, the following method may be used: a method in which the rate of evaporation is increased by adding fine metal particles or the like to the evaporation source.

The blending ratio between materials for the photoelectric conversion film 3 is expressed on a weight basis in the case of the coating method or on a volume basis in the case of the vapor deposition method. In particular, in the coating method, the blending ratio is determined using the weight of each material used to prepare a solution. In the vapor deposition method, the blending ratio between the materials is determined in such a manner that the thickness of a layer of each deposited material is monitored with a thickness meter during vapor deposition.

At least one of the upper electrode 4 and the lower electrode 2 is a transparent electrode made of a conducting material transparent to near-infrared light. A bias voltage is applied to each of the lower electrode 2 and the upper electrode 4 through a wiring line (not shown). For example, the polarity of the bias voltage is set such that, among charges generated in the photoelectric conversion film 3, electrons move to the upper electrode 4 and holes move to the lower electrode 2. Alternatively, the polarity of the bias voltage may be set such that, among the charges generated in the photoelectric conversion film 3, holes move to the upper electrode 4 and electrons move to the lower electrode 2.

The bias voltage is preferably applied such that the electric field generated in the photoelectric conversion element 10A, that is, the value obtained by dividing the applied voltage by the distance between the lower electrode 2 and the upper electrode 4 is within a range of $1.0 \times 10^3$ V/cm to $1.0 \times 10^7$ V/cm and may be applied such that the value is within a range of $1.0 \times 10^4$ V/cm to $1.0 \times 10^7$ V/cm. Adjusting the magnitude of the bias voltage as described above allows charges to efficiently move to the upper electrode 4, thereby enabling signals to be extracted outside depending on the charges.

A material for the lower electrode 2 and the upper electrode 4 may be a transparent conducting oxide (TCO) which has high transmittance for light in the near-infrared region and low resistance. A metal thin film made of Au or the like can be used as a transparent electrode and has an extremely increased resistance in some cases as compared to a transparent electrode that is prepared so as to have a transmittance of 60% to 80% in order to obtain a transmittance of 90% or more for light in the near-infrared region. Therefore, the TCO is more effective in obtaining transparent electrodes which are highly transparent to near-infrared light and which have low resistance than metal materials such as Au. Examples of the TCO include, but are not limited to, indium tin oxide (ITO), indium zinc oxide (IZO), aluminum-doped zinc oxide (AZO), fluorine-doped tin oxide (FTO), $SnO_2$, $TiO_2$, and $ZnO_2$. The lower electrode 2 and the upper electrode 4 may be prepared in such a manner that the TCO and a metal material such as Au are appropriately used alone or in combination depending on desired transmittance.

The material for the lower electrode 2 and the upper electrode 4 is not limited to the above-mentioned conducting material transparent to near-infrared light and may be another material.

Various methods are used to prepare the lower electrode 2 and the upper electrode 4 depending on a material used. In the case of using, for example, ITO, the following method may be used: an electron beam method, a sputtering method, a resistive heating evaporation method, a chemical reaction method such as a sol-gel method, a coating method using a dispersion of indium tin oxide, or the like. In this case, after an ITO film is formed, the ITO film may be subjected to a UV-ozone treatment, a plasma treatment, or the like.

According to the photoelectric conversion element 10A, photoelectric conversion is induced in the photoelectric conversion film 3 by near-infrared light entering the photoelectric conversion film 3 through the support substrate 1 and the lower electrode 2. This allows holes and electrons of generated hole-electron pairs to be collected by the lower electrode 2 and the upper electrode 4, respectively. Thus, near-infrared light entering the photoelectric conversion element 10A can be detected by measuring, for example, the potential of the lower electrode 2.

The photoelectric conversion element 10A may further include an electron-blocking layer 5 and hole-blocking layer 6 described below. The injection of electrons into the photoelectric conversion film 3 from the lower electrode 2 and the injection of holes into the photoelectric conversion film 3 from the upper electrode 4 can be suppressed by sandwiching the photoelectric conversion film 3 between the electron-blocking layer 5 and the hole-blocking layer 6. This enables the dark current to be reduced. Incidentally, the electron-blocking layer 5 and the hole-blocking layer 6 are described below and therefore are not described in detail herein.

Next, another example of the photoelectric conversion element according to this embodiment is described with reference to FIGS. 1B and 2. FIG. 1B is the schematic sectional view of the photoelectric conversion element 10B, which is an example of the photoelectric conversion element according to this embodiment. FIG. 2 shows an example of the schematic energy band of the photoelectric conversion element 10B, which has a configuration shown in FIG. 1B.

Figure 1B:
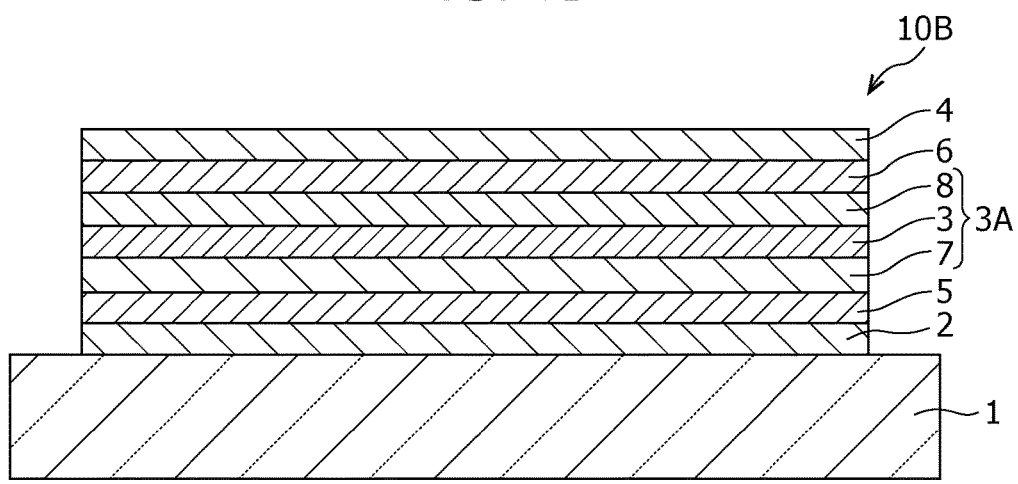
FIG. 1B is a schematic sectional view of an example of a photoelectric conversion element according to another embodiment of the present disclosure.
Figure 2:
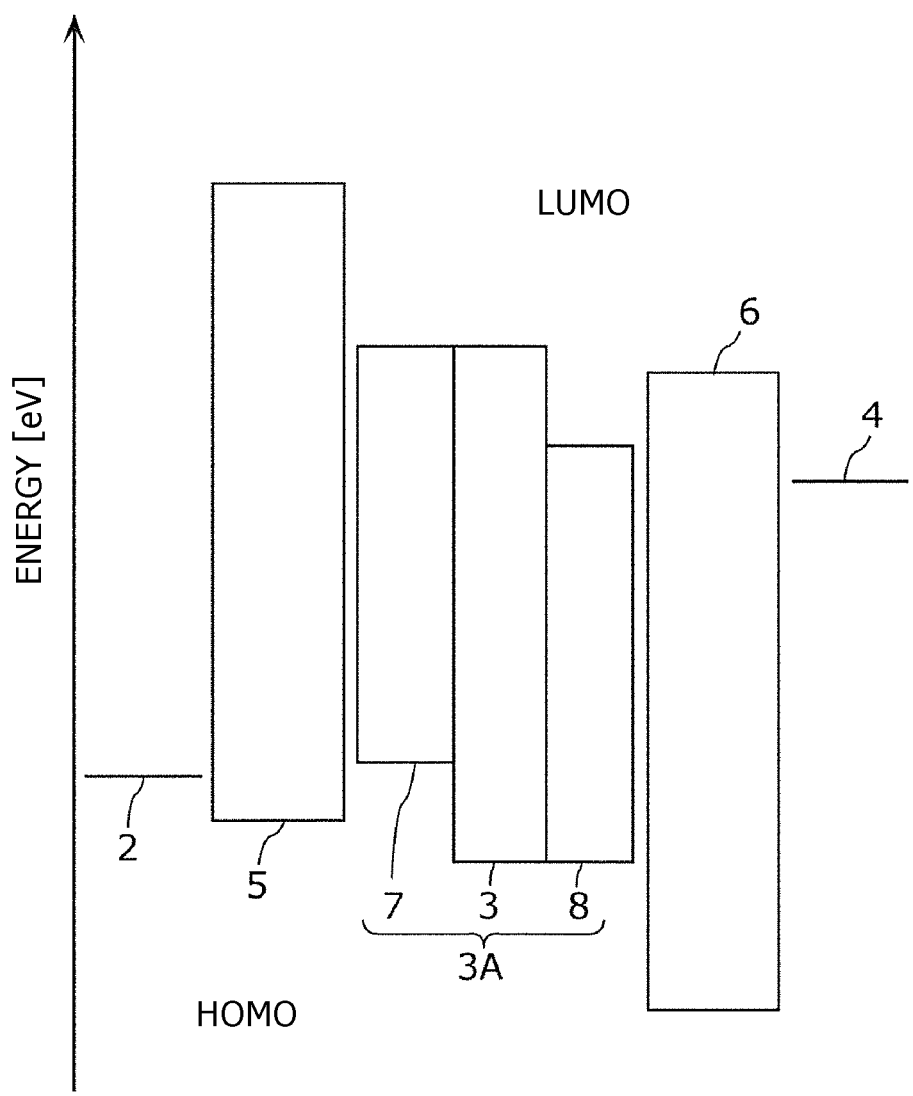
FIG. 2 is a graph showing the illustrative energy band of the photoelectric conversion element shown in FIG. 1B.

In the photoelectric conversion element 10B, which is shown in FIG. 1B, the same components as those of the photoelectric conversion element 10A, which is shown in FIG. 1A, are given the same reference numerals.

As shown in FIG. 1B, the photoelectric conversion element 10B includes a lower electrode 2, an upper electrode 4, and a photoelectric conversion layer 3A placed between the lower electrode 2 and the upper electrode 4. The photoelectric conversion layer 3A includes, for example, a photoelectric conversion film 3, a p-type semiconductor layer 7 functioning as a hole transport layer, and an n-type semiconductor layer 8 functioning as an electron transport layer. The photoelectric conversion film 3 is placed between the p-type semiconductor layer 7 and the n-type semiconductor layer 8. The photoelectric conversion element 10B further includes an electron-blocking layer 5 placed between the lower electrode 2 and the photoelectric conversion layer 3A and a hole-blocking layer 6 placed between the upper electrode 4 and the photoelectric conversion layer 3A. Incidentally, the photoelectric conversion film 3 is as described above and therefore is not described in detail herein.

The photoelectric conversion layer 3A includes the photoelectric conversion film 3, the p-type semiconductor layer 7, and the n-type semiconductor layer 8. At least one of a p-type semiconductor contained in the p-type semiconductor layer 7 and an n-type semiconductor contained in the n-type semiconductor layer 8 may be an organic semiconductor below.

The photoelectric conversion layer 3A may contain the above composition and at least one of the p-type semiconductor and the n-type semiconductor.

The photoelectric conversion layer 3A may include a bulk heterojunction structure layer containing the p-type semiconductor and the n-type semiconductor. When the photoelectric conversion layer 3A includes the bulk heterojunction structure layer, a disadvantage that the carrier diffusion length in the photoelectric conversion layer 3A is short can be compensated for and the photoelectric conversion efficiency can be increased.

In the photoelectric conversion layer 3A, the bulk heterojunction structure layer may be placed between the p-type semiconductor layer 7 and the n-type semiconductor layer 8. Sandwiching the bulk heterojunction structure layer between the p-type semiconductor layer 7 and the n-type semiconductor layer 8 allows the rectification of holes and electrons to be higher than that in the bulk heterojunction structure layer and reduces the loss due to the recombination of charge-separated holes and electrons; hence, higher photoelectric conversion efficiency can be obtained. The bulk heterojunction structure layer is as described in Japanese Patent No. 5553727, in which a bulk hetero-type active layer is described in detail.

In the bulk heterojunction structure layer, charges are generated in a dark state in some cases because the p-type semiconductor and the n-type semiconductor are in contact with each other. Therefore, the dark current can be reduced by reducing the contact between the p-type semiconductor and the n-type semiconductor. When the bulk heterojunction structure layer contains a large amount of the n-type semiconductor, such as a fullerene derivative, from the viewpoint of charge mobility, the element resistance can be reduced. In this case, the volume ratio and weight ratio of the n-type semiconductor to the p-type semiconductor in the bulk heterojunction structure layer may be 4 or more. However, when the proportion of the p-type semiconductor in the bulk heterojunction structure layer is small, the sensitivity in the near-infrared region is low. Therefore, the volume ratio of the n-type semiconductor to the p-type semiconductor in the bulk heterojunction structure layer is preferably not too large from the viewpoint of sensitivity and may be, for example, 20 or less. When the volume ratio of the n-type semiconductor to the p-type semiconductor in the bulk heterojunction structure layer is 4 to 20, both of the reduction of the dark current and the sensitivity in the near-infrared region can be achieved (see Japanese Unexamined Patent Application Publication No. 2016-225456).

A p-type organic semiconductor is a donor organic semiconductor, is mainly typified by a hole-transporting organic compound, and refers to an organic compound having the property of donating an electron. In particular, the p-type organic semiconductor refers to one of two organic compounds that has lower ionization potential in the case where the two organic compounds are used in contact with each other. Thus, the donor organic semiconductor used may be any organic compound having an electron-donating property. For example, the following compounds can be used: triarylamine compounds; benzidine compounds; pyrazoline compounds; styrylamine compounds; hydrazone compounds; triphenylmethane compounds; carbazole compounds; polysilane compounds; thiophene compounds; phthalocyanine compounds; cyanine compounds; merocyanine compounds; oxonol compounds; polyamine compounds; indole compounds; pyrrole compounds; pyrazole compounds; polyarylene compounds; condensed aromatic compounds such as naphthalene derivatives, anthracene derivatives, phenanthrene derivatives, tetracene derivatives, pyrene derivatives, perylene derivatives, and fluoranthene derivatives; and metal complexes containing a nitrogen-containing heterocyclic compound as a ligand. The donor organic semiconductor used is not limited to these compounds and may be an organic compound with an ionization potential lower than that of an organic compound used as an acceptor organic semiconductor as described above.

An n-type organic semiconductor is an acceptor organic semiconductor, is mainly typified by an electron-transporting organic compound, and refers to an organic compound having the property of accepting an electron. In particular, the n-type organic semiconductor refers to one of two organic compounds that has higher electron affinity in the case where the two organic compounds are used in contact with each other. Thus, the acceptor organic compound used may be any organic compound having an electron-accepting property. For example, the following compounds are cited: fullerene; fullerene derivatives; condensed aromatic compounds such as naphthalene derivatives, anthracene derivatives, phenanthrene derivatives, tetracene derivatives, pyrene derivatives, perylene derivatives, and fluoranthene derivatives; nitrogen-, oxygen-, and/or sulfur-containing five- to seven-membered heterocyclic compounds such as pyridine, pyrazine, pyrimidine, pyridazine, triazine, quinoline, quinoxaline, quinazoline, phthalazine, cinnoline, isoquinoline, pteridine, acridine, phenazine, phenanthroline, tetrazole, pyrazole, imidazole, thiazole, oxazole, indazole, benzimidazole, benzotriazole, benzoxazole, benzothiazole, carbazole, purine, triazolopyridazine, triazolopyrimidine, tetrazaindene, oxadiazole, imidazopyridine, pyrrolidine, pyrrolopyridine, thiadiazolopyridine, dibenzazepine, and tribenzazepine; polyarylene compounds; fluorenone compounds; cyclopentadiene compounds; silyl compounds; and metal complexes containing a nitrogen-containing heterocyclic compound as a ligand. The acceptor organic semiconductor used is not limited to these compounds and may be an organic compound with an electron affinity higher than that of an organic compound used as a donor organic semiconductor as described above.

The electron-blocking layer 5 is placed to reduce the dark current due to the injection of electrons from the lower electrode 2 and suppresses the injection of electrons into the photoelectric conversion layer 3A from the lower electrode 2. The electron-blocking layer 5 may contain the above-mentioned p-type semiconductor or hole-transporting organic compound. As shown in FIG. 2, the electron-blocking layer 5 has a HOMO energy level lower than that of the p-type semiconductor layer 7 of the photoelectric conversion layer 3A and a LUMO energy level higher than that of the p-type semiconductor layer 7 of the photoelectric conversion layer 3A. In other words, the photoelectric conversion layer 3A has a HOMO energy level higher than that of the electron-blocking layer 5 and a LUMO energy level lower than that of the electron-blocking layer 5 in the vicinity of the interface between the photoelectric conversion layer 3A and the electron-blocking layer 5.

The hole-blocking layer 6 is placed to reduce the dark current due to the injection of holes from the upper electrode 4 and suppresses the injection of holes into the photoelectric conversion layer 3A from the upper electrode 4. A material for the hole-blocking layer 6 may be, for example, an organic substance such as 3,4,9,10-perylenetetracarboxylic dianhydride (PTCDA) or bathocuproine (BCP); an organic-metal compound such as copper phthalocyanine, an acetylacetonate complex, or tris(8-quinolinolato) aluminum (Alq); or an inorganic substance such as MgAg or MgO. The hole-blocking layer 6 may have high transmittance for near-infrared light, may contain a material having no absorption in the visible region, and may have a small thickness so as not to prevent the light absorption of the photoelectric conversion film 3. The thickness of the hole-blocking layer 6 depends on the configuration of the photoelectric conversion layer 3A, the thickness of the upper electrode 4, or the like and may be, for example, 2 nm to 50 nm. The hole-blocking layer 6 may contain the above-mentioned n-type semiconductor or electron-transporting organic compound.

In the case of using the electron-blocking layer 5, the material for the lower electrode 2 is selected from the above-mentioned materials in consideration of adhesion to the electron-blocking layer 5, electron affinity, ionization potential, stability, and the like. This applies to the upper electrode 4.

As shown in FIG. 2, when the work function of the upper electrode 4 is relatively large (for example, 4.8 eV), a barrier to the movement of holes to the photoelectric conversion film 3 during the application of a bias voltage is low. Therefore, the holes are readily injected into the photoelectric conversion layer 3A from the upper electrode 4 and, as a result, it is conceivable that the dark current is large. In this embodiment, the presence of the hole-blocking layer 6 reduces the dark current.

Imaging Device

Figure 3:
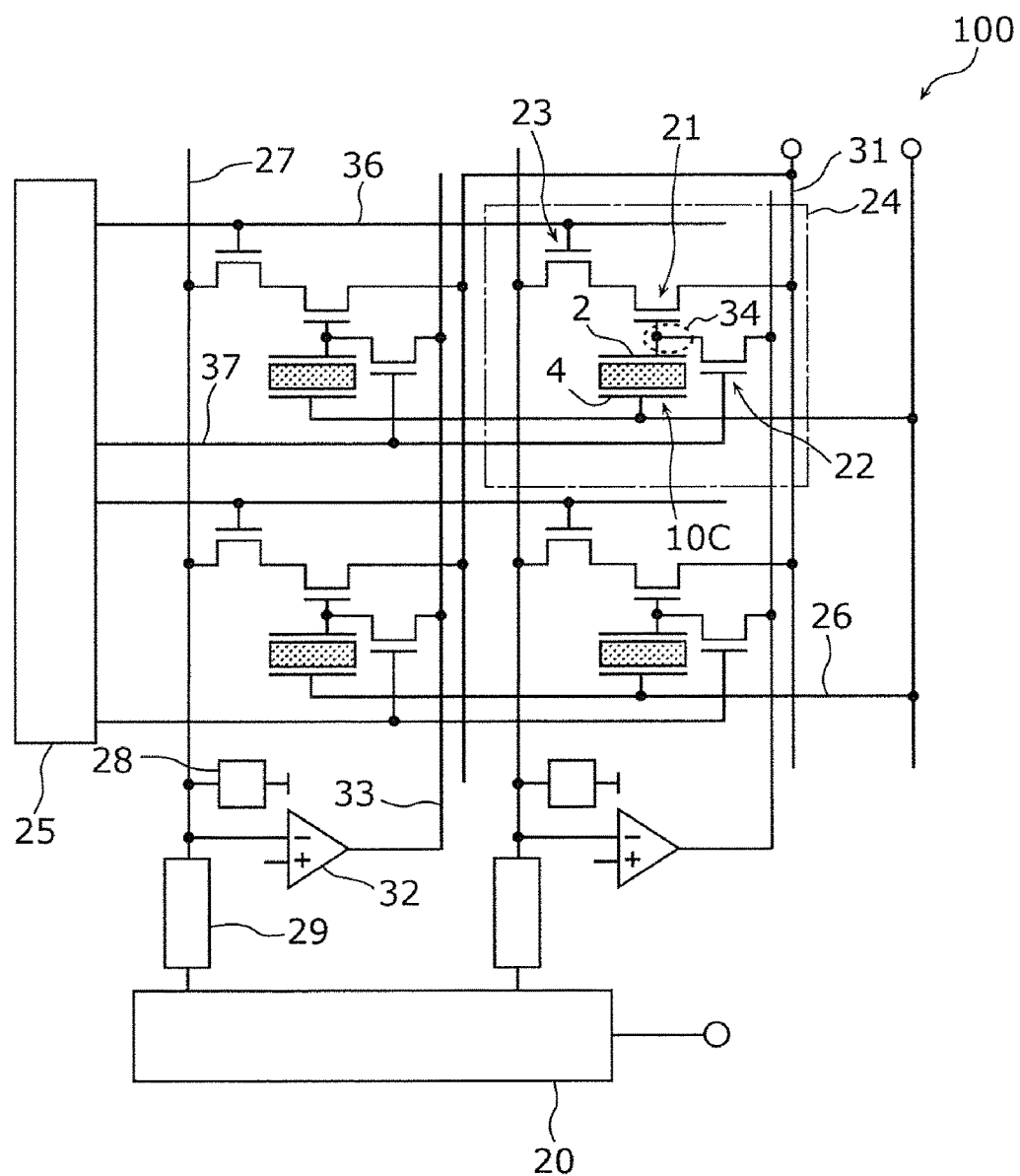
FIG. 3 is a diagram illustrating an example of the circuit configuration of an imaging device according to an embodiment of the present disclosure.
Figure 4:
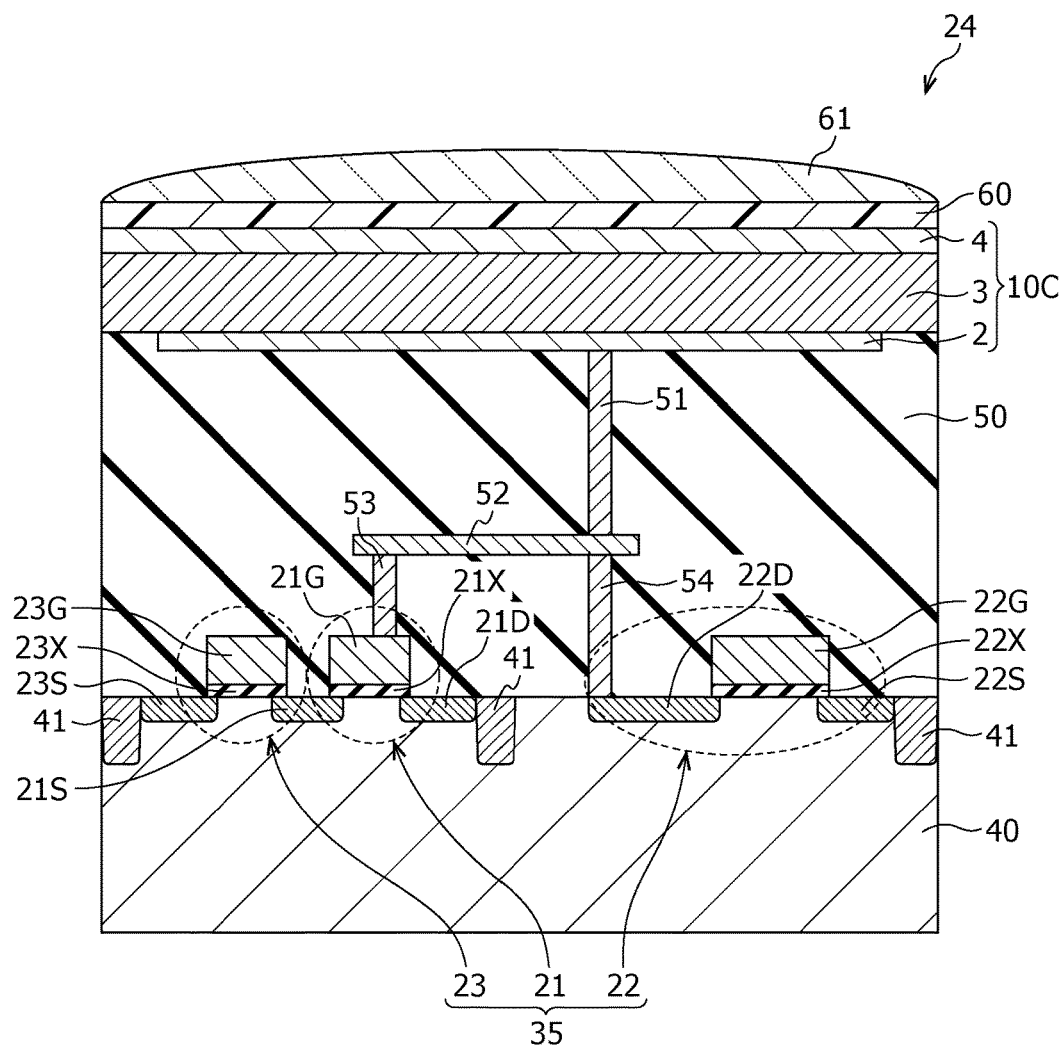
FIG. 4 is a schematic sectional view of an example of the device structure of a unit pixel cell in the imaging device.

An imaging device 100 according to an embodiment of the present disclosure is described with reference to FIGS. 3 and 4. FIG. 3 is a diagram illustrating an example of the circuit configuration of the imaging device 100. FIG. 4 is a schematic sectional view of an example of the device structure of a unit pixel cell 24 in the imaging device 100.

The imaging device 100 includes a substrate (hereinafter referred to as the semiconductor substrate 40) and unit pixel cells 24 each including a charge detection circuit 35 attached to the semiconductor substrate 40, a photoelectric conversion section 10C placed on the semiconductor substrate 40, and a charge storage node 34 electrically connected to the charge detection circuit 35 and the photoelectric conversion section 10C. The photoelectric conversion section 10C of each unit pixel cell 24 includes the above-mentioned photoelectric conversion element 10A or 10B.

As shown in FIG. 3, the imaging device 100 includes the unit pixel cells 24 and peripheral circuits. The imaging device 100 is an organic image sensor implemented in the form of a one-chip integrated circuit and includes a pixel array including the two-dimensionally arranged unit pixel cells 24.

The unit pixel cells 24 are arranged dimensionally, that is, in row and column directions, on the semiconductor substrate 40 to form a photosensitive region which is a pixel region. FIG. 3 shows an example in which the unit pixel cells 24 are arranged in a matrix with two rows and two columns. In FIG. 3, a circuit (for example, a pixel electrode control circuit) for individually setting the sensitivity of the unit pixel cells 24 is not shown for convenience of illustration. The imaging device 100 may be a line sensor. In this case, the unit pixel cells 24 may be one-dimensionally arranged. The terms "row direction" and "column direction" as used herein refer to the direction in which a row extends and the direction in which a column extends, respectively. That is, a vertical direction is a column direction and a horizontal direction is a row direction.

Each unit pixel cell 24 includes the charge storage node 34, which is electrically connected to the photoelectric conversion section 10C and the charge detection circuit 35. The charge detection circuit 35 includes an amplification transistor 21, a reset transistor 22, and an address transistor 23.

The photoelectric conversion section 10C includes a lower electrode 2 placed as a pixel electrode and an upper electrode 4 placed as a counter electrode. The photoelectric conversion section 10C may include the above-mentioned photoelectric conversion element 10A or 10B. A predetermined bias voltage is applied to the upper electrode 4 through a counter electrode signal line 26.

The lower electrode 2 is connected to a gate electrode 21G of the amplification transistor 21. Signal charges collected by the lower electrode 2 are stored in the charge storage node 34. The charge storage node 34 is located between the lower electrode 2 and the gate electrode 21G of the amplification transistor 21. In this embodiment, signal charges are holes. Signal charges may be electrons.

The signal charges stored in the charge storage node 34 are applied to the gate electrode 21G of the amplification transistor 21 in the form of a voltage corresponding to the amount of signal charges. The amplification transistor 21 amplifies this voltage, which is selectively read out as a signal voltage by the address transistor 23. The reset transistor 22 includes source/drain electrodes connected to the lower electrode 2 and resets the signal charges stored in the charge storage node 34. In other words, the reset transistor 22 resets the potential of the gate electrode 21G of the amplification transistor 21 and the potential of the lower electrode 2.

In order to selectively perform the above-mentioned operations in the unit pixel cells 24, the imaging device 100 includes power supply lines 31, vertical signal lines 27, address signal lines 36, and reset signal lines 37 and these lines are connected to each unit pixel cell 24. In particular, the power supply lines 31 are connected to source/drain electrodes of the amplification transistor 21 and the vertical signal lines 27 are connected to source/drain electrodes of the address transistor 23. Each address signal line 36 is connected to a gate electrode 23G of the address transistor 23. Each reset signal line 37 is connected to a gate electrode 22G of the reset transistor 22.

The peripheral circuits include a vertical scanning circuit 25, a horizontal signal read-out circuit 20, a plurality of column signal-processing circuits 29, a plurality of load circuits 28, and a plurality of differential amplifiers 32. The vertical scanning circuit 25 is also referred to as a row scanning circuit. The horizontal signal read-out circuit 20 is also referred to as a column scanning circuit. The column signal-processing circuits 29 are also referred to as row signal accumulation circuits. The differential amplifiers 32 are also referred to as feed-back amplifiers.

The vertical scanning circuit 25 is connected to the address signal lines 36 and the reset signal lines 37, selects the unit pixel cells 24 placed in each row on a row basis, reads out the signal voltage, and resets the potential of the lower electrode 2. The power supply lines 31 are source follower power supplies and supply a predetermined power supply voltage to each unit pixel cell 24. The horizontal signal read-out circuit 20 is electrically connected to the column signal-processing circuits 29. The column signal-processing circuits 29 are electrically connected to the unit pixel cells 24 placed in each column through the vertical signal lines 27 corresponding to the column. Each of the load circuits 28 is electrically connected to a corresponding one of the vertical signal lines 27. The load circuits 28 and the amplification transistors 21 form source follower circuits.

The differential amplifiers 32 are placed so as to correspond to each column. A negative-side input terminal of each of the differential amplifiers 32 is connected to a corresponding one of the vertical signal lines 27. Output terminals of the differential amplifiers 32 are connected to the unit pixel cells 24 through feed-back lines 33 corresponding to the column.

The vertical scanning circuit 25 applies row selection signals controlling the turning on and off of the address transistors 23 to the gate electrodes 23G of the address transistors 23 through the address signal lines 36. This allows a row that is intended to be read out to be scanned and selected. Signal voltages are read out from the unit pixel cells 24 in the selected row to the vertical signal lines 27. Furthermore, the vertical scanning circuit 25 applies reset signals controlling the turning on and off of the reset transistors 22 to the gate electrodes 22G of the reset transistors 22 through the reset signal lines 37. This allows a row of the unit pixel cells 24 that are intended to be reset to be selected. The vertical signal lines 27 transmit the signal voltages read out from the unit pixel cells 24 selected by the vertical scanning circuit 25 to the column signal-processing circuits 29.

The column signal-processing circuits 29 perform noise reduction signal processing typified by correlated double sampling, analog-digital conversion (A-D conversion), and the like.

The horizontal signal read-out circuit 20 sequentially reads out signals from the column signal-processing circuits 29 to a horizontal common signal line (not shown).

The differential amplifiers 32 are connected to the drain electrodes of the reset transistors 22 through the feed-back lines 33. Thus, when the address transistors 23 and the reset transistors 22 are in the conduction state, negative terminals of the differential amplifiers 32 receive outputs from the address transistors 23. The differential amplifiers 32 perform a feed-back operation such that the gate potential of each amplification transistor 21 is equal to a predetermined feed-back voltage. In this operation, the output voltage of each differential amplifier 32 is equal to 0 V or a positive voltage close to 0 V. The term "feed-back voltage" refers to the output voltage of the differential amplifier 32.

As shown in FIG. 4, each unit pixel cell 24 includes the semiconductor substrate 40, the charge detection circuit 35, the photoelectric conversion section 10C, and the charge storage node 34.

The semiconductor substrate 40 may be an insulating substrate provided with a semiconductor layer placed on a surface on the side where the photosensitive region is formed and is, for example, a p-type silicon substrate. The semiconductor substrate 40 includes impurity regions (herein, n-type regions) 21D, 21S, 22D, 22S, and 23S and an isolation region 41 for electrically separating the unit pixel cells 24. The isolation region 41 is placed between the impurity regions 21D and the impurity regions 22D. This suppresses the leakage of the signal charges stored in the charge storage node 34. The isolation region 41 is formed by, for example, the implantation of acceptor ions under predetermined conditions.

The impurity regions 21D, 21S, 22D, 22S, and 23S are typically diffusion layers formed in the semiconductor substrate 40. As shown in FIG. 4, the amplification transistor 21 includes the impurity regions 21S and 21D and the gate electrode 21G. The impurity region 21S and the impurity region 21D function as, for example, a source region and drain region, respectively, of the amplification transistor 21. A channel region of the amplification transistor 21 is formed between the impurity regions 21S and 21D.

Likewise, the address transistor 23 includes the impurity regions 23S and 21S and the gate electrode 23G, which is connected to one of the address signal lines 36. In this example, the amplification transistor 21 and the address transistor 23 share the impurity region 21S and therefore are electrically connected to each other. The impurity region 23S functions as, for example, a source region of the address transistor 23. The impurity region 23S has a connection to one of the vertical signal lines 27 as shown in FIG. 3.

The reset transistor 22 includes the impurity regions 22D and 22S and the gate electrode 22G, which is connected to one of the reset signal lines 37. The impurity region 22S functions as, for example, a source region of the reset transistor 22. The impurity region 22S has a connection to one of the reset signal lines 37 as shown in FIG. 3.

An interlayer insulating layer 50 is placed on the semiconductor substrate 40 so as to cover the amplification transistor 21, the address transistor 23, and the reset transistor 22.

Wiring layers (not shown) may be placed in the interlayer insulating layer 50. The wiring layers are formed typically from a metal such as copper and may partly include, for example, wiring lines such as the above-mentioned vertical signal lines 27. The number of insulating layers in the interlayer insulating layer 50 and the number of the wiring layers placed in the interlayer insulating layer 50 can be arbitrarily set.

The following components are placed in the interlayer insulating layer 50: a contact plug 54 connected to the impurity region 22D of the reset transistor 22, a contact plug 53 connected to the gate electrode 21G of the amplification transistor 21, a contact plug 51 connected to the lower electrode 2, and a wiring line 52 connecting the contact plugs 51, 54, and 53 together. This electrically connects the impurity region 22D of the reset transistor 22 to the gate electrode 21G of the amplification transistor 21.

The charge detection circuit 35 detects signal charges captured by the lower electrode 2 and outputs a signal voltage. The charge detection circuit 35 includes the amplification transistor 21, the reset transistor 22, and the address transistor 23 and is attached to the semiconductor substrate 40.

The amplification transistor 21 is placed in the semiconductor substrate 40 and includes the impurity region 21D, which functions as a drain electrode; the impurity region 21S, which functions as a source electrode; a gate insulating layer 21X placed on the semiconductor substrate 40; and the gate electrode 21G, which is placed on the gate insulating layer 21X.

The reset transistor 22 is placed in the semiconductor substrate 40 and includes the impurity region 22D, which functions as a drain electrode; the impurity region 22S, which functions as a source electrode; a gate insulating layer 22X placed on the semiconductor substrate 40; and the gate electrode 22G, which is placed on the gate insulating layer 22X.

The address transistor 23 is placed in the semiconductor substrate 40 and includes the impurity region 21S, which functions as a drain electrode; the impurity region 23S, which functions as a source electrode; a gate insulating layer 23X placed on the semiconductor substrate 40; and the gate electrode 23G, which is placed on the gate insulating layer 23X. The impurity region 21S is shared by the amplification transistor 21 and the address transistor 23, whereby the amplification transistor 21 and the address transistor 23 are connected in series.

The above-mentioned photoelectric conversion section 10C is placed on the interlayer insulating layer 50. In other words, in this embodiment, the unit pixel cells 24, which form the pixel array, are arranged on the semiconductor substrate 40. The unit pixel cells 24, which are two-dimensionally arranged on the semiconductor substrate 40, form the photosensitive region. The distance (pixel pitch) between the two neighboring unit pixel cells 24 may be, for example, about 2 μm.

The photoelectric conversion section 10C includes the above-mentioned photoelectric conversion element 10A or 10B.

The photoelectric conversion section 10C is overlaid with a color filter 60. The color filter 60 is overlaid with a micro-lens 61. The color filter 60 is, for example, an on-chip color filter formed by patterning and is made of a photosensitive resin containing a dye or pigment dispersed therein or a similar resin. The micro-lens 61 is placed in the form of, for example, an on-chip micro-lens and is made of an ultraviolet photosensitive material or the like.

The imaging device 100 can be manufactured by a general semiconductor manufacturing process. In particular, when the semiconductor substrate 40 used is a silicon substrate, various silicon semiconductor processes can be used to manufacture the imaging device 100.

From the above, according to the present disclosure, the following element and device can be obtained: a photoelectric conversion element and imaging device, having high light absorption characteristics in the near-infrared region, capable of exhibiting high photoelectric conversion efficiency.

EXAMPLES

Compositions and photoelectric conversion elements according to the present disclosure are described below in detail with reference to examples. The present disclosure is not in any way limited to the examples.

A photoelectric conversion film formed from a composition containing a compound obtained in Example 1 is referred to as Example 2. A photoelectric conversion film formed from a composition containing a compound obtained in Comparative Example 1 is referred to as Comparative Example 3. A photoelectric conversion film formed from a composition containing a compound obtained in Comparative Example 2 is referred to as Comparative Example 4. A photoelectric conversion element including the photoelectric conversion film obtained in Example 2 is referred to as Example 3. A photoelectric conversion element including the photoelectric conversion film obtained in Comparative Example 3 is referred to as Comparative Example 5. A photoelectric conversion element including the photoelectric conversion film obtained in Comparative Example 4 is referred to as Comparative Example 6.

Hereinafter, $C_2H_5$ is represented by Et, $C_3H_7$ is represented by Pr, $iC_3H_7$ is represented by iPr, $C_4H_9$ is represented by Bu, $C_6H_{13}$ is represented by Hex, $C_{10}H_{21}$ is represented by Dec, and $C_{48}H_{26}N_8$ is represented by Nc in some cases.

Example 1

Synthesis of $(OEt)_8Sn(OSiHex)_3)_2Nc$

A compound, $(OEt)_8Sn(OSiHex)_3)_2Nc$, represented by the following formula was synthesized in accordance with Steps (1) to (4) below:

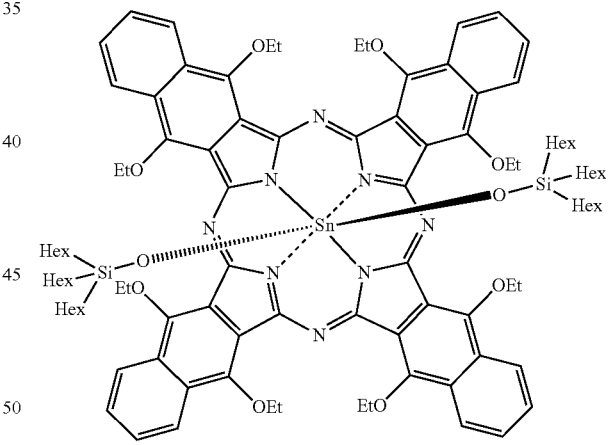

(1) Synthesis of
1,4-Diethoxy-2,3-naphthalocyaninedicarbonitrile

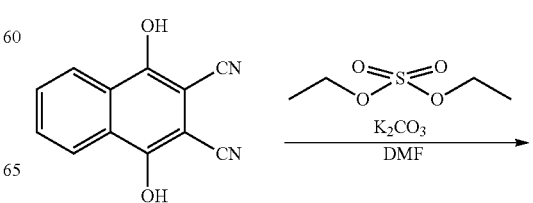

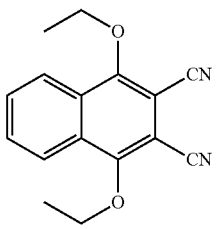

To a 100 mL reaction vessel, 3.0 g of 1,4-diethoxy-2,3-naphthalenedicarbonitrile, 4.54 g of potassium carbonate, 15 mL of dehydrated dimethylformamide, and 5.06 g of diethyl sulfate were added, followed by stirring at 110° C. for 20 hours under an Ar atmosphere. After the completion of reaction was confirmed by thin layer chromatography (TLC), the reaction vessel was cooled to room temperature. After cooling, city water was added to the reaction vessel, followed by separatory washing. Thereafter, a solid was obtained by distilling off a solvent. The obtained solid was dissolved in dichloromethane, followed by drying with sodium sulfate. After sodium sulfate was filtered off, a filtrate was concentrated under vacuum. Obtained residue was vacuum-dried at 40° C., whereby 3.47 g of 1,4-diethoxy-2,3-naphthalocyaninedicarbonitrile was obtained. The yield in this step was 91%.

(2) Synthesis of $(OEt)_8H_2Nc$

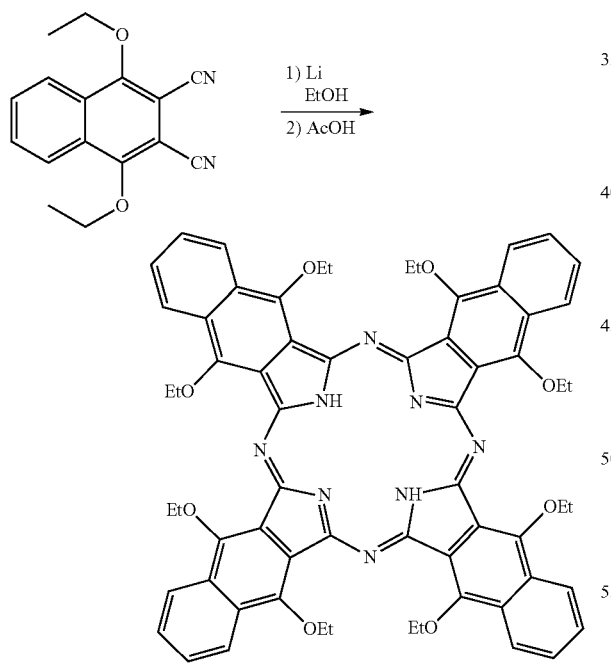

To a 50 mL reaction vessel, 1.0 g of 1,4-diethoxy-2,3-naphthalocyaninedicarbonitrile synthesized in Step (1) and 15 mL of dehydrated ethanol were added under an Ar atmosphere, followed by dissolution by heating at 70° C. Thereafter, 0.25 g of lithium particles were added to the reaction vessel, followed by stirring at 70° C. for 24 hours under heating reflux. After the completion of reaction was confirmed by TLC, the reaction vessel was cooled to room temperature. After cooling, the reaction vessel was quenched by adding 10 mL of acetic acid thereto, followed by stirring for 7 hours.

An obtained reaction liquid was concentrated under vacuum, whereby residue was obtained. The obtained residue was dissolved in a dichloromethane-pyridine (3:1) solution, followed by adding city water and then separatory washing. An organic layer obtained by a liquid separation operation was dried with magnesium sulfate. After magnesium sulfate was filtered off, a filtrate was concentrated under vacuum, whereby a crude product was obtained.

After the obtained crude product was purified by silica gel column chromatography, a concentrate of an obtained fraction was suspended and washed with methanol, followed by filtration. An obtained filter cake was vacuum-dried at 60° C., whereby 547.2 mg of $(OEt)_8H_2Nc$ was obtained. The yield in this step was 54%.

(3) Synthesis of $(OEt)_8SnBr_2Nc$

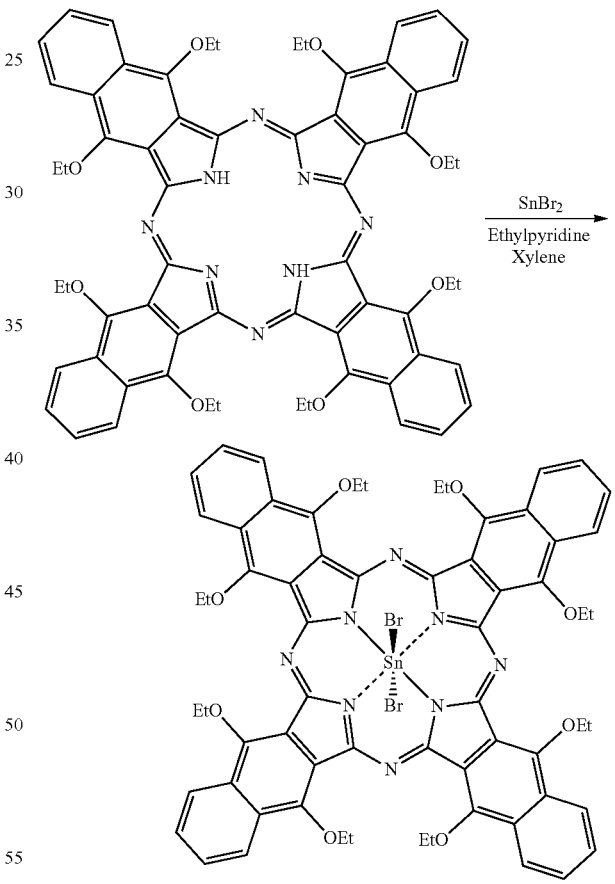

To a 50 mL reaction vessel, 0.2 g of $(OEt)_8SnBr_2Nc$ synthesized in Step (2), 1.02 g of tin bromide, 14 mL of xylene, and 1.4 mL of 2-ethylpyridine were added under an Ar atmosphere, followed by stirring at 200° C. for 20 hours under heating reflux. After the completion of reaction was confirmed by TLC, the reaction vessel was cooled to room temperature. An obtained reaction liquid was concentrated under vacuum, whereby a black solid was obtained. A concentrate containing the obtained black solid was suspended and washed with methanol, followed by filtration.

An obtained filter cake was vacuum-dried at 60° C., whereby 78.5 mg of (OEt)$_8$SnBr$_2$Nc was obtained. The yield in this step was 31%.

(4) Synthesis of (OEt)$_8$Sn(OSiHex$_3$)$_2$Nc

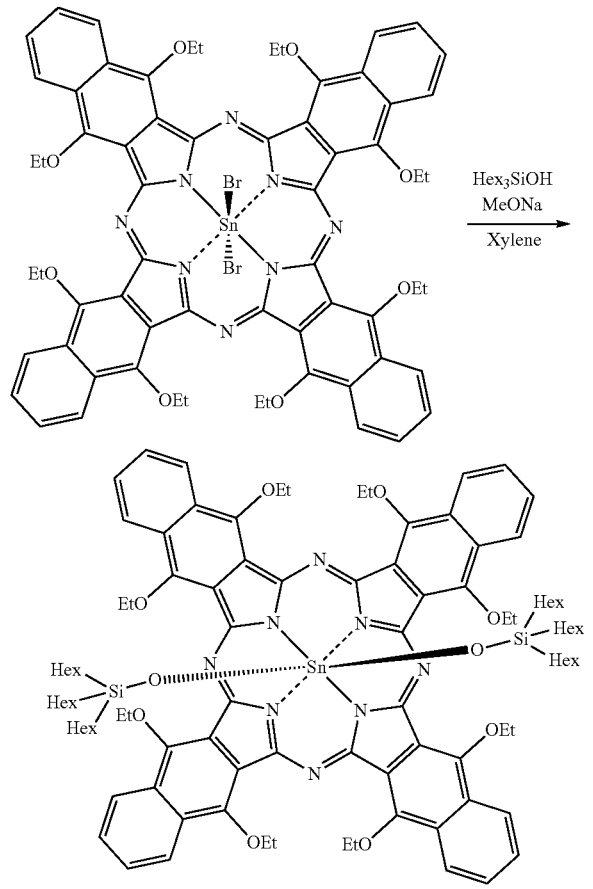

To a 20 mL reaction vessel, 0.1 mL of trihexylsilanol and 5 mL of xylene were added under an Ar atmosphere, followed by dissolution by stirring. Thereafter, 10 mg of sodium methoxide was added to the reaction vessel, followed by stirring at 100° C. for 1 hour under heating reflux. Next, after the reaction vessel was cooled to room temperature, 30 mg of (OEt)$_8$SnBr$_2$Nc synthesized in Step (3) was added thereto, followed by stirring at 160° C. for 44 hours. After the completion of reaction was confirmed by TLC, an obtained reaction liquid was cooled to room temperature. After cooling, the reaction liquid was concentrated under vacuum, methanol was added to obtained residue, and the residue was suspended and washed, followed by filtration. An obtained filter cake was vacuum-dried at 60° C., whereby 28.2 mg of (OEt)$_8$Sn(OSi(C$_6$H$_{13}$)$_3$)$_2$Nc was obtained. The yield in this step was 70%.

An obtained compound was identified by proton nuclear magnetic resonance spectroscopy ($^1$H-NMR) and matrix-assisted laser desorption ionization-time of flight mass spectrometry (MALDI-TOF-MS). Results are described below.

$^1$H-NMR (400 MHz, C$_6$D$_6$): δ (ppm)=9.11 (8H), 7.66 (8H), 5.61 (16H), 1.89 (24H), 0.69 (12H), 0.43 (42H), −0.17 (12H), −1.14 (12H)

MALDI-TOF-MS measured value: m/z=1,781.4 [M$^+$]

The chemical formula of the target compound (OEt)$_8$Sn(OSiHex$_3$)$_2$Nc is C$_{100}$H$_{134}$N$_6$O$_{10}$Si$_2$Sn and the exact mass thereof is 1,782.88.

From the above results, it could be confirmed that the target compound was obtained by the above synthesis procedure.

Comparative Example 1

Synthesis of (OBu)$_8$Sn(OSiHex$_3$)$_3$)$_2$Nc

A compound, (OBu)$_8$Sn(OSiHex$_3$)$_3$)$_2$Nc, represented by the following formula was synthesized in accordance with Steps (1) to (3) below:

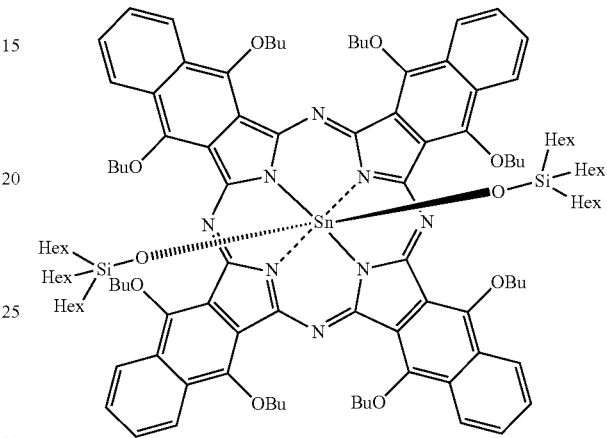

(1) Synthesis of (OBu)$_8$H$_2$Nc

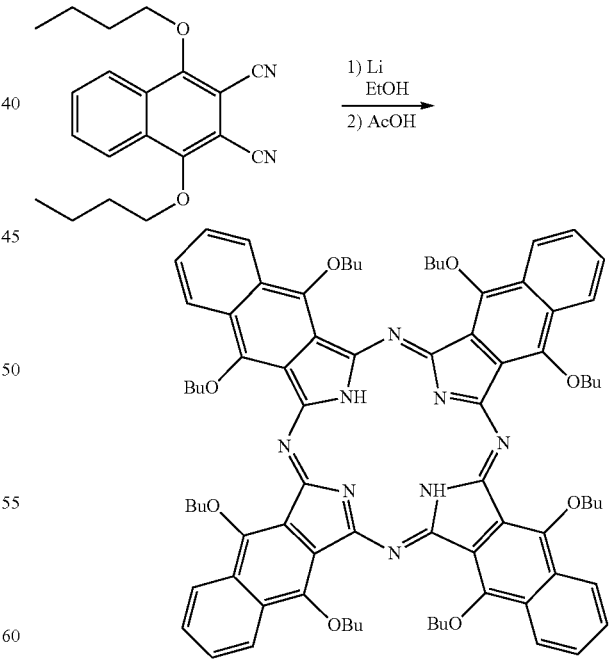

To a 200 mL reaction vessel, 4.0 g of 1,4-dibutoxy-2,3-naphthalocyaninedicarbonitrile synthesized in a similar way to Step (1) of Example 1 and 40 mL of 1-butanol were added under an Ar atmosphere, followed by dissolution by heating at 70° C. Thereafter, 1.0 g of lithium particles were added in small amounts to the reaction vessel, followed by stirring at for 1.5 hours under heating reflux. After the reaction vessel was cooled to room temperature, the reaction vessel was quenched by adding 40 mL of acetic acid thereto, followed by stirring overnight.

An obtained reaction liquid was concentrated under vacuum, whereby residue was obtained. The obtained residue was dissolved in 320 mL of a dichloromethane-pyridine (3:1) solution, followed by adding city water and then separatory washing. An organic layer obtained by a liquid separation operation was dried with magnesium sulfate. After magnesium sulfate was filtered off, a filtrate was concentrated under vacuum, whereby a crude product was obtained.

After the obtained crude product was purified by silica gel column chromatography, a concentrate of an obtained fraction was suspended and washed with methanol, followed by filtration. An obtained filter cake was vacuum-dried at 60° C., whereby 1.9 g of $(OBu)_8H_2Nc$ was obtained. The yield in this step was 48%.

(2) Synthesis of $(OBu)_8SnBr_2Nc$

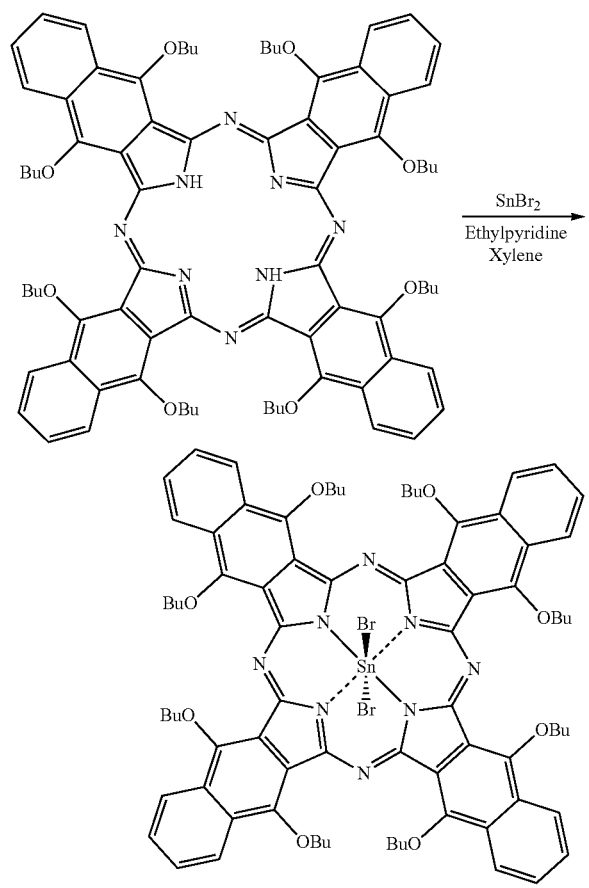

To a 500 mL reaction vessel, 2.1 g of $(OBu)_8H_2Nc$ synthesized in Step (1), 9.17 g of tin bromide, 152 mL of xylene, and 15 mL of 2-ethylpyridine were added under an Ar atmosphere, followed by stirring at 200° C. for 21 hours under heating reflux. Next, after the reaction vessel was cooled to room temperature, the reaction vessel was quenched by adding 40 mL of acetic acid thereto, followed by stirring overnight. After the completion of reaction was confirmed by TLC, the reaction vessel was cooled to room temperature. An obtained reaction liquid was concentrated under vacuum, followed by dissolving obtained residue by adding toluene to the residue. After the residue dissolved in toluene was filtered using Celite®, a filtrate was concentrated under vacuum, whereby 5.2 g of a crude product was obtained. The obtained crude product was purified with Bio-Beads and a concentrate of an obtained fraction was suspended and washed with methanol, followed by filtration. An obtained filter cake was vacuum-dried at 60° C., whereby 1.8 g of $(OBu)_8SnBr_2Nc$ was obtained. The yield in this step was 69%.

(3) Synthesis of $(OBu)_8Sn(OSiHex_3)_2Nc$

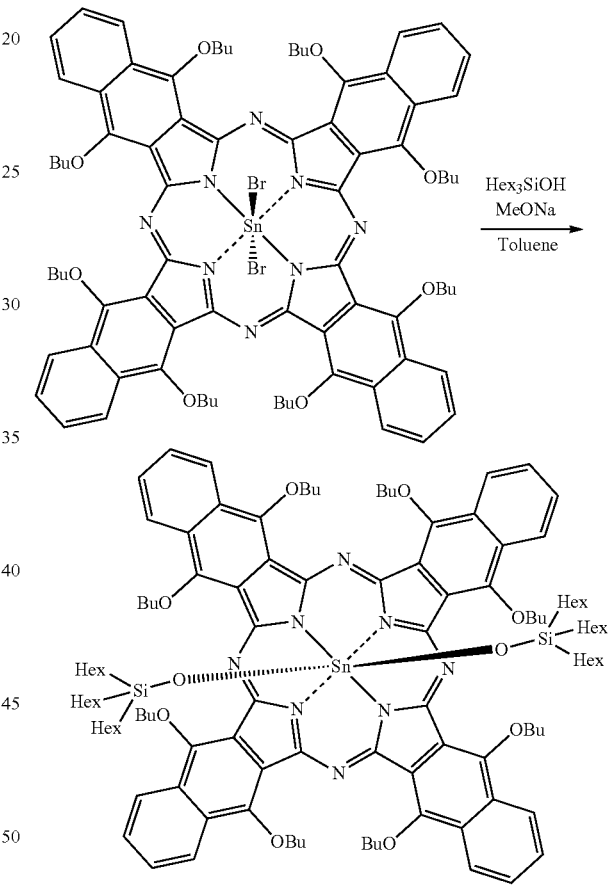

To a 500 mL reaction vessel, 6.16 mL of trihexylsilanol and 300 mL of toluene were added under an Ar atmosphere, followed by dissolution by stirring. Thereafter, 616 mg of sodium methoxide was added to the reaction vessel, followed by stirring at 100° C. for 1 hour under heating reflux. Next, after the reaction vessel was cooled to room temperature, 1.8 g of $(OBu)_8SnBr_2Nc$ synthesized in Step (2) was added thereto, followed by stirring at 150° C. for 8 hours under heating reflux. After the reaction vessel was cooled to room temperature, an obtained reaction liquid was concentrated under vacuum. Methanol was added to obtained residue, followed by suspension washing and then filtration. An obtained filter cake was vacuum-dried at 60° C., whereby 3.27 g of a crude product was obtained.

The obtained crude product was purified with activated alumina. A concentrate of an obtained fraction was suspended and washed with methanol, followed by filtration. An obtained filter cake was vacuum-dried at 60° C., whereby 2.1 g of $(OBu)_8Sn(OSiHex_3)_2Nc$ was obtained. The yield in this step was 89%.

An obtained compound was identified by $^1$H-NMR and MALDI-TOF-MS. Results are described below.

$^1$H-NMR (400 MHz, $C_6D_6$): δ (ppm)=9.20 (8H), 7.67 (8H), 5.61 (16H), 2.45 (16H), 1.78 (16H), 1.11 (24H), 0.68 (12H), 0.43 (42H), −0.15 (12H), −1.09 (12H)

MALDI-TOF-MS measured value: m/z=2,007.04 [M$^+$]

The chemical formula of the target compound $(OBu)_8Sn(OSiHex_3)_2Nc$ is $C_{116}H_{166}N_6O_{10}Si_2Sn$ and the exact mass thereof is 2,007.13.

From the above results, it could be confirmed that the target compound was obtained by the above synthesis procedure.

Comparative Example 2

Synthesis of $Sn(OSiHex_3)_2Nc$

A compound, $Sn(OSiHex_3)_2Nc$, represented by the following formula was synthesized in accordance with Steps (1) to (3) below:

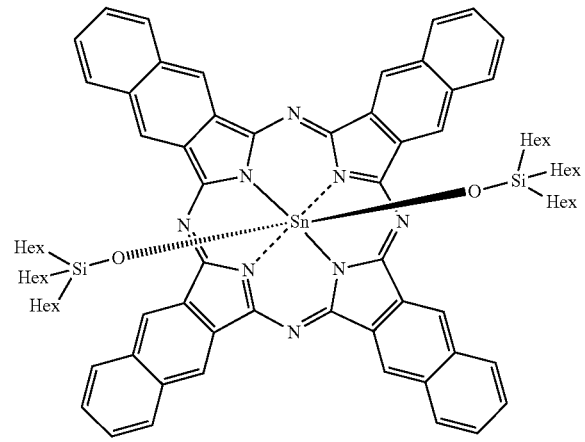

(1) Synthesis of $(C_6H_{13})_3SiOH$

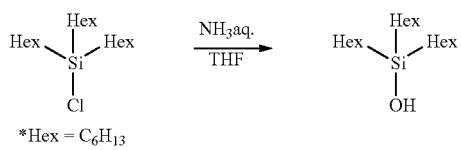

*Hex = $C_6H_{13}$

In a three-necked flask, 15 g of $SiCl(C_6H_{13})_3$ and 75 mL of THF were put. The three-necked flask was put in a cooling bath and was cooled to 10° C. or lower. In a dropping funnel, 75 ml of ammonia water was poured, followed by adding the full amount of ammonia water dropwise to the three-necked flask over a period of 10 minutes and then stirring at room temperature for 2 hours.

Next, 150 mL of ethyl acetate and 150 mL of city water were added to the three-necked flask, followed by stirring for 10 minutes and then separating liquids using a separatory funnel. To a separated water phase, 150 mL of ethyl acetate was added, followed by extracting a reaction product in the water phase with ethyl acetate. The extraction with ethyl acetate was performed twice. To an organic layer obtained by the extraction, 150 mL of a saturated aqueous solution of ammonium chloride was added, followed by separatory washing three times. Thereafter, 150 mL of city water was added to the organic layer, followed by separatory washing once. Subsequently, 150 mL of saturated salt water was added to the organic layer, followed by separatory washing. After an organic layer obtained by washing was dried with magnesium sulfate, magnesium sulfate was filtered off. An obtained filtrate was concentrated under vacuum and obtained residue was vacuum-dried at 60° C., whereby 13.8 g of $(C_6H_{13})_3SiOH$ was obtained.

The yield in this step was 97%.

(2) Synthesis of $Sn(OH)_2Nc$

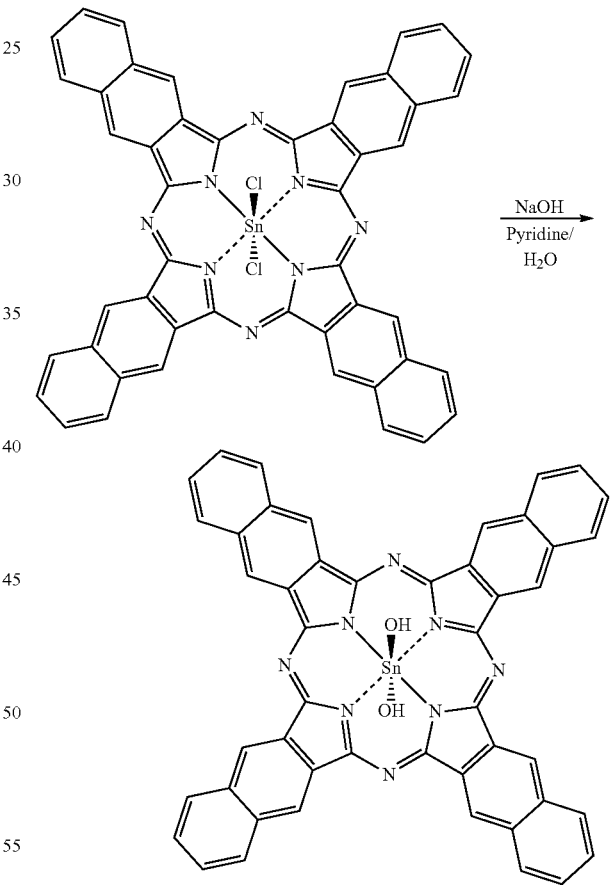

To a three-necked flask, 6.2 g of $SnCl_2Nc$, 1.1 g of sodium hydroxide, 45 mL of pyridine, and 90 mL of distilled water were added in that order, followed by heating reflux at 100° C. for 25 hours. After heating, the three-necked flask was cooled to room temperature. An obtained reaction liquid was concentrated under vacuum and an obtained crude product was filtered out. After 300 mL of distilled water was added to an obtained filter cake and the obtained filter cake was suspended and washed with distilled water, a solid was filtered out. The obtained solid was vacuum-dried at 40° C. for 5 hours, whereby 7.5 g of Sn(OH)$_2$Nc was obtained. The yield in this step was 86%.

(3) Synthesis of Sn(OSiHex$_3$)$_2$Nc

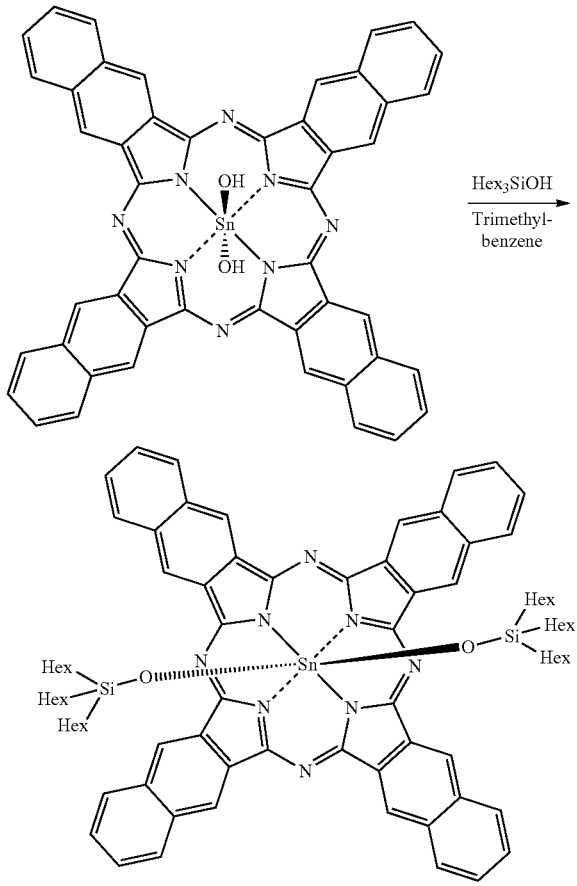

A 500 mL three-necked flask equipped with a ribbon heater and a cooling tube was placed. In the three-necked flask, 5.1 g of Sn(OH)$_2$Nc synthesized in Step (2), 13.8 g of (C$_6$H$_{13}$)$_3$SiOH synthesized in Step (1), and 450 mL of 1,2,4-trimethylbenzene were put, followed by heating and stirring at 200° C. for 3 hours. The three-necked flask was cooled to room temperature and was then cooled at 0° C. for about 3 hours, whereby a target substance was precipitated, followed by filtering out the target substance. A solid of the obtained target substance was suspended and washed with 100 mL of ethanol twice. The ethanol used for washing was washed with 50 mL of acetone and the target substance in the ethanol was reprecipitated, followed by filtering out the target substance. The solid of the obtained target substance was vacuum-dried at 120° C. for 3 hours, whereby 6.9 g of Sn(OSiHex$_3$)$_2$Nc was obtained. The yield in this step was 82%.

An obtained compound was identified by $^1$H-NMR and MALDI-TOF-MS. Results are described below.

$^1$H-NMR (400 MHz, C$_6$D$_6$): δ (ppm)=10.2 (8H), 8.27 (8H), 7.47 (8H), 0.68 (12H), 0.5-0.2 (42H), −0.42 (12H), −1.42 (12H)

MALDI-TOF-MS measured value: m/z=1,428.69 [M$^+$]

The chemical formula of the target compound Sn(OSiHex$_3$)$_2$Nc is C$_{84}$H$_{102}$N$_6$O$_2$Si$_2$Sn and the exact mass thereof is 1,430.7.

From the above results, it could be confirmed that the target compound was obtained by the above synthesis procedure.

Example 2

Figure 5A:
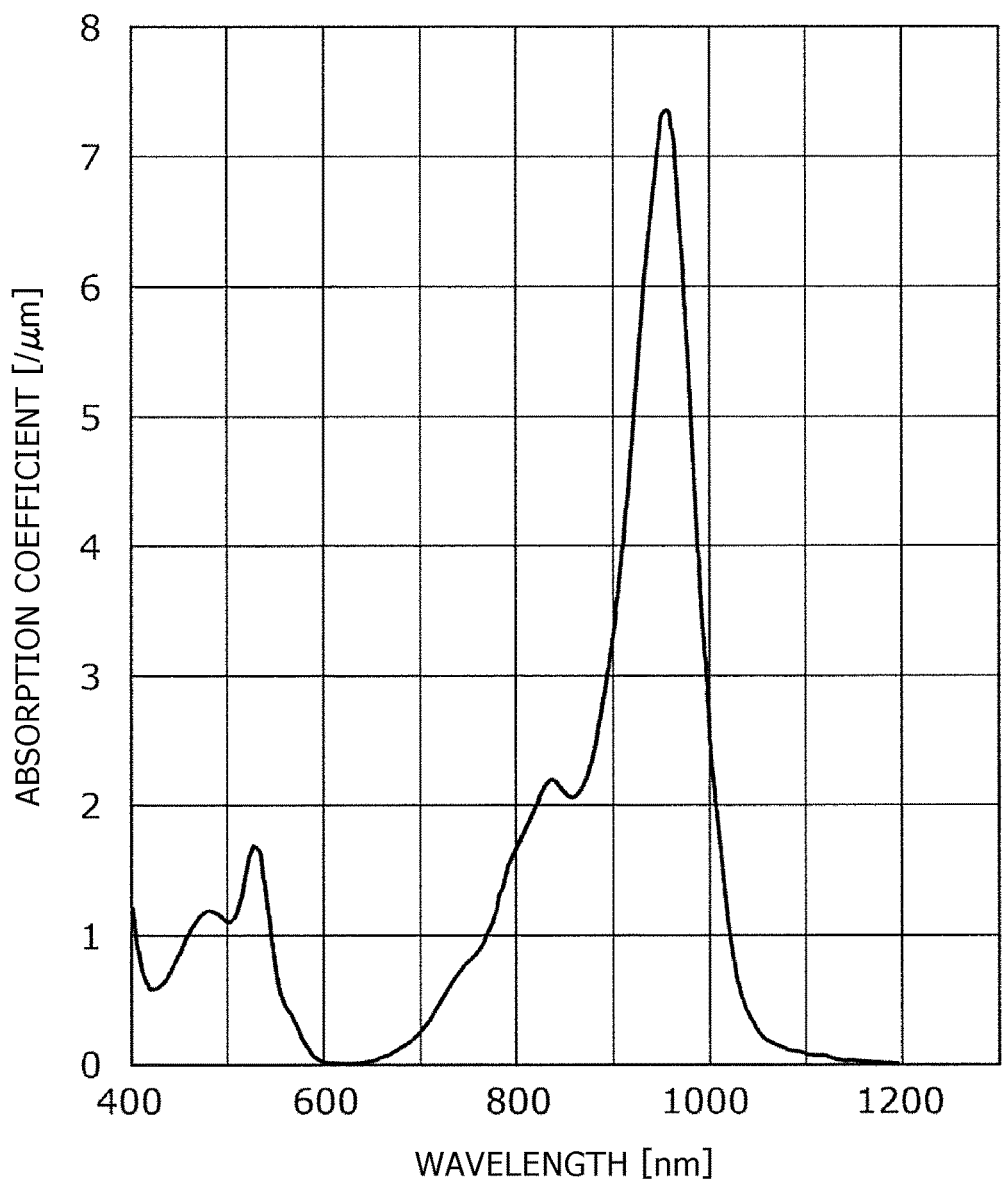
FIG. 5A is a graph showing the absorption spectrum of a photoelectric conversion film obtained in Example 2.

A support substrate, made of quartz glass, having a thickness of 0.7 mm was used. A composition containing (OEt)$_8$Sn(OSiHex$_3$)$_2$Nc obtained in Example 1 was applied to the support substrate by a spin coating method, whereby a photoelectric conversion film having a thickness of 100 nm was obtained. The absorption spectrum of the obtained photoelectric conversion film is shown in FIG. 5A.

Comparative Example 3

Figure 5B:
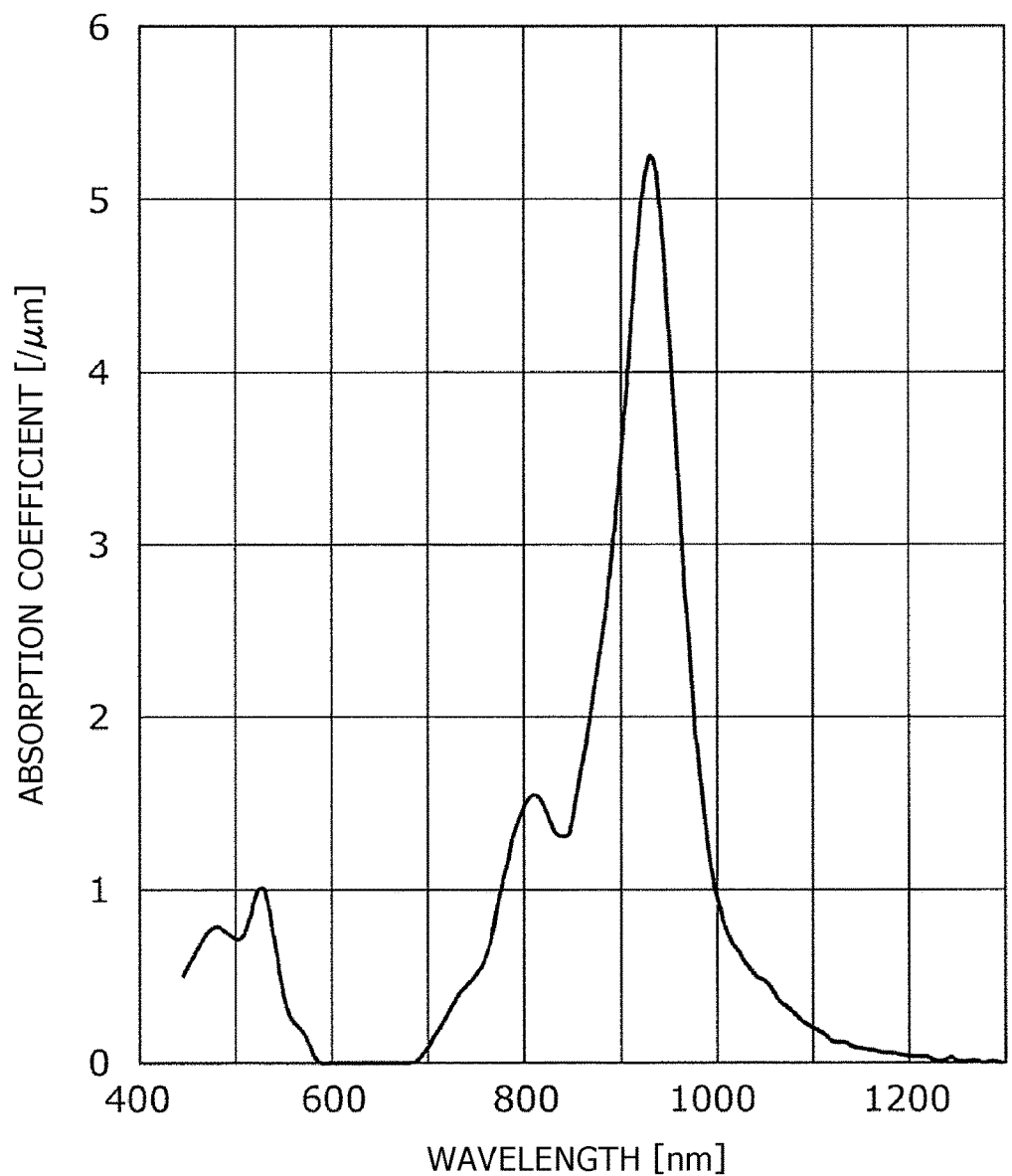
FIG. 5B is a graph showing the absorption spectrum of a photoelectric conversion film obtained in Comparative Example 3.

A photoelectric conversion film was obtained in substantially the same manner as that used in Example 2 except that a composition containing (OBu)$_8$Sn(OSiHex$_3$)$_2$Nc obtained in Comparative Example 1 was used. The absorption spectrum of the obtained photoelectric conversion film is shown in FIG. 5B.

Comparative Example 4

Figure 5C:
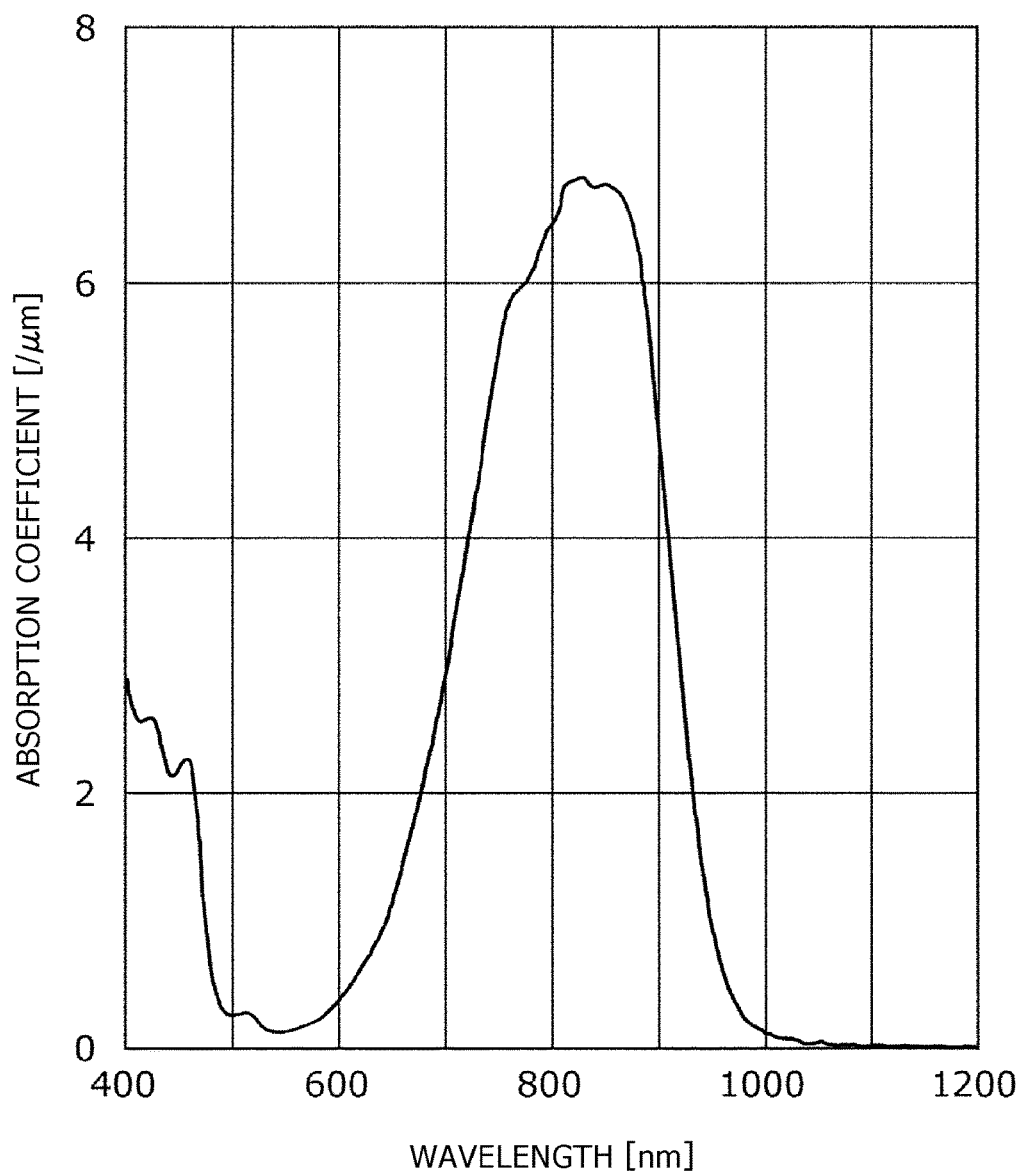
FIG. 5C is a graph showing the absorption spectrum of a photoelectric conversion film obtained in Comparative Example 4.

A support substrate, made of quartz glass, having a thickness of 0.7 mm was used. A composition containing Sn(OSiHex$_3$)$_2$Nc obtained in Comparative Example 2 was applied to the support substrate by a vacuum vapor deposition method, whereby a photoelectric conversion film was obtained. The absorption spectrum of the obtained photoelectric conversion film is shown in FIG. 5C.

Measurement of Absorption Spectrum

The photoelectric conversion films obtained in Example 2, Comparative Example 3, and Comparative Example 4 were measured for absorption spectrum using a spectrophotometer, U4100, available from Hitachi High-Technologies Corporation. The wavelength measured for absorption spectrum was 400 nm to 1,200 nm.

As shown in FIG. 5A, the photoelectric conversion film obtained in Example 2 had an absorption peak appearing at about 950 nm. The absorption efficiency of the absorption peak was about 7.4/μm.

As shown in FIG. 5B, the photoelectric conversion film obtained in Comparative Example 3 had an absorption peak appearing at about 920 nm. The absorption efficiency of the absorption peak was about 5.2/μm.

As shown in FIG. 5C, the photoelectric conversion film obtained in Comparative Example 4 had an absorption peak appearing at about 820 nm. The absorption efficiency of the absorption peak was about 6.8/μm.

As described above, the photoelectric conversion film obtained in Example 2 had an absorption peak appearing at the longest wavelength and the highest absorption efficiency among the three photoelectric conversion films.

Comparing materials for the three photoelectric conversion films shows that differences in absorption characteristics between the photoelectric conversion films are caused by whether a naphthalocyanine skeleton has an α-chain and the difference in number of carbon atoms in an alkyl moiety of an alkoxy group of the α-chain.

In Example 2, the composition containing the compound (OEt)$_8$Sn(OSiHex$_3$)$_2$Nc obtained in Example 1 is used as a material for the photoelectric conversion film. In Comparative Example 3, the composition containing the compound (OBu)$_8$Sn(OSiHex$_3$)$_2$Nc obtained in Comparative Example 1 is used as a material for the photoelectric conversion film.

In Comparative Example 4, the composition containing the compound $Sn(OSiHex_3)_2Nc$ obtained in Comparative Example 2 is used as a material for the photoelectric conversion film.

From the chemical structures of these materials and results of the absorption spectra, it can be confirmed that containing a compound having a naphthalocyanine skeleton with an α-alkoxy group like Example 2 and Comparative Example 3 causes the increase of the wavelength having sensitivity to near-infrared light. Furthermore, from the fact that Example 2 has an absorption peak at a longer wavelength as compared to Comparative Example 3, it can be confirmed that as the number of carbon atoms in an alkyl moiety of an alkoxy group is smaller, the wavelength having sensitivity to near-infrared light is longer.

Example 3

A substrate used was a glass substrate, provided with a 150 nm ITO electrode, having a thickness of 0.7 mm. The ITO electrode was used as a lower electrode. A photoelectric conversion layer was formed on the ITO electrode using a mixture of $(OEt)_8Sn(OSiHex_3)_2Nc$ obtained in Example 1 and a [6,6]-phenyl-$C_{61}$-butyric acid methyl ester (PCBM) derivative so as to have a thickness of 250 nm. Furthermore, an Al electrode serving as an upper electrode was formed on the photoelectric conversion film so as to have a thickness of 80 nm. The Al electrode was formed at a deposition rate of 1 angstrom per second in a vacuum of $5.0 \times 10^{-4}$ Pa or less. Spectral sensitivity characteristics of an obtained photoelectric conversion element were measured. The obtained spectral sensitivity characteristics are shown with a continuous line in FIG. 6.

Comparative Example 5

A photoelectric conversion element was obtained in substantially the same manner as that used in Example 3 except that $(OBu)_8Sn(OSiHex_3)_2Nc$ obtained in Comparative Example 1 was used to form a photoelectric conversion layer. Spectral sensitivity characteristics of the obtained photoelectric conversion element are shown with a dotted line in FIG. 6.

Comparative Example 6

A photoelectric conversion element was obtained in substantially the same manner as that used in Example 3 except that $Sn(OSiHex_3)_2Nc$ obtained in Comparative Example 2 and fullerene were used to form a photoelectric conversion layer. Spectral sensitivity characteristics of the obtained photoelectric conversion element are shown with a dashed line in FIG. 6.

Measurement of Spectral Sensitivity

The photoelectric conversion elements obtained in Example 3, Comparative Example 5, and Comparative Example 6 were measured for spectral sensitivity using a long wavelength-sensitive spectral sensitivity measurement device, CEP-25RR, available from Bunkoukeiki Co., Ltd. The above photoelectric conversion elements were introduced into a measurement jig capable of being hermetically sealed in a glove box under a nitrogen atmosphere and were measured.

Figure 6:
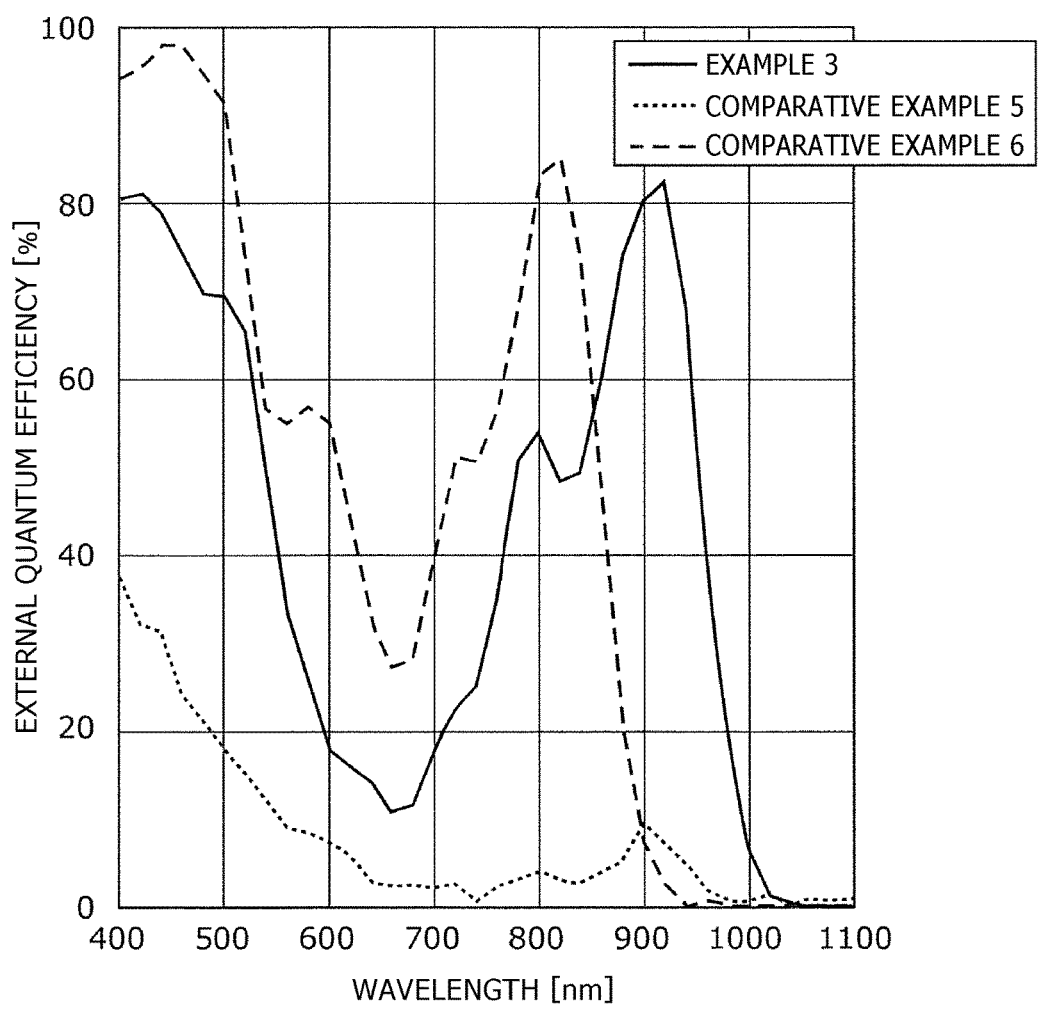
FIG. 6 is a graph showing measurement results of spectral sensitivity characteristics of a photoelectric conversion element obtained in each of Example 3, Comparative Example 5, and Comparative Example 6.

As shown in FIG. 6, the external quantum efficiency of the photoelectric conversion element obtained in Example 3 is highest, about 82%, at a wavelength of about 920 nm. The photoelectric conversion element obtained in Example 5 has high external quantum efficiency in a wide range of the near-infrared region, particularly in a wavelength range from about 680 nm to 1,050 nm.

The external quantum efficiency of the photoelectric conversion element obtained in Comparative Example 5 is highest, less than 10%, at a wavelength of 900 nm. The external quantum efficiency thereof gives a broad peak in the near-infrared region, which ranges from about 750 nm to 950 nm. The external quantum efficiency thereof is low, about a few percent.

The external quantum efficiency of the photoelectric conversion element obtained in Comparative Example 6 is highest, about 84%, at a wavelength of about 820 nm. However, the external quantum efficiency thereof, as well as that obtained in Comparative Example 5, is less than 10% at a wavelength of about 900 nm and is lower than that obtained in Comparative Example 5.

As described above, the photoelectric conversion element obtained in Example 3 has high external quantum efficiency at the longest wavelength among the three photoelectric conversion elements and also has relatively high external quantum efficiency at a wavelength of 900 nm or more. However, in Comparative Examples 5 and 6, no high external quantum efficiency is obtained at a wavelength of 900 nm or more and the external quantum efficiency is 0% at a wavelength of 950 nm or more.

In Example 3, a composition containing the compound $(OEt)_8Sn(OSiHex_3)_2Nc$ obtained in Example 1 is used as a material for the photoelectric conversion film. In Comparative Example 5, a composition containing the compound $(OBu)_8Sn(OSiHex_3)_2Nc$ obtained in Comparative Example 1 is used as a material for the photoelectric conversion film. In Comparative Example 6, a composition containing the compound $Sn(OSiHex_3)_2Nc$ obtained in Comparative Example 2 is used as a material for the photoelectric conversion film.

From the chemical structures of these materials and results of the external quantum efficiency, it is clear that when a naphthalocyanine skeleton has an α-chain like Example 3 and Comparative Example 5, the external quantum efficiency peaks at long wavelengths of 900 nm or more. From results of Example 3 and Comparative Example 5, it is clear that when the number of carbon atoms in the α-chain of the naphthalocyanine skeleton is 2, high external quantum efficiency is obtained. This is probably because as the number of carbon atoms in an α-chain is smaller, the efficiency of charge transfer from a naphthalocyanine derivative to an acceptor material is higher.

A compound according to the present disclosure is composed of a naphthalocyanine ring which is a basic skeleton, axial ligands, and an α-chain. The naphthalocyanine ring has a planar structure, in which the axial ligands extend perpendicularly to a plane. In Comparative Example 6, high quantum efficiency is obtained. Therefore, the axial ligands probably have no influence on electron transfer. In the case of introducing the α-chain, as the number of carbon atoms is smaller, the quantum efficiency is higher. Therefore, it is conceivable that the transfer of electrons from a naphthalocyanine derivative to an acceptor material occurs outside the naphthalocyanine ring. Hence, it is probably advantageous that the number of carbon atoms in the α-chain is small.

SUMMARY

As described above, the photoelectric conversion films obtained in Example 2, Comparative Example 3, and Comparative Example 4 and the photoelectric conversion elements obtained in Example 3, Comparative Example 5, and Comparative Example 6 were measured for light absorption characteristics and photoelectric conversion efficiency for near-infrared light. As a result, it could be confirmed that the increase in wavelength of sensitivity to near-infrared light and high external quantum efficiency could be achieved using a composition containing (OEt)$_8$Sn(OSiHex$_3$)$_2$Nc, which had a naphthalocyanine skeleton with an α-chain containing two carbon atoms.

Synthesis Examples

Synthesis examples of other compounds having an α-chain with an ethylene group, which contains two carbon atoms, are described below.

Synthesis Example 1

Synthesis of (OC$_2$H$_5$)$_8$Sn(OSi(C$_{10}$H$_{21}$)$_3$)$_2$Nc

A compound, (OC$_2$H$_5$)$_8$Sn(OSi(C$_{10}$H$_{21}$)$_3$)$_2$Nc, represented by the following formula was synthesized in accordance with Steps (1) to (4) below:

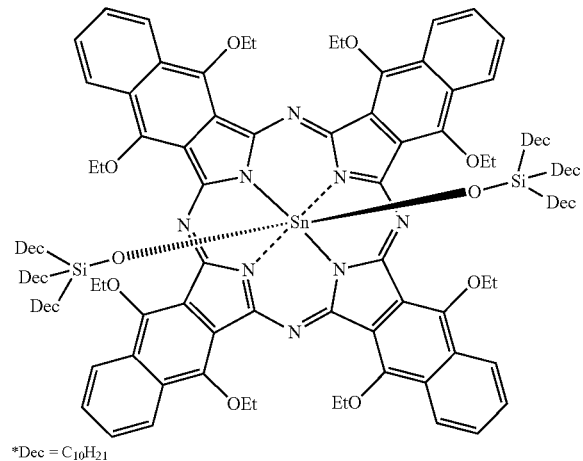

*Dec = C$_{10}$H$_{21}$

Steps (1) to (3) through which (OC$_2$H$_5$)$_8$SnBr$_2$Nc was synthesized were performed in the same manner as that used in Example 1.

(4) Synthesis of (OC$_2$H$_5$)$_8$Sn(OSi(C$_{10}$H$_{21}$)$_3$)$_2$Nc

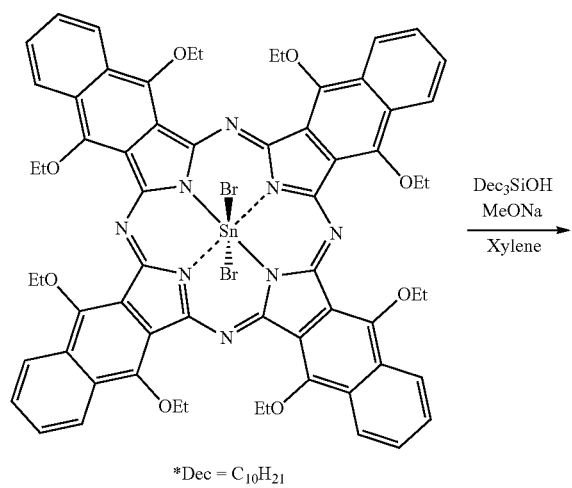

*Dec = C$_{10}$H$_{21}$

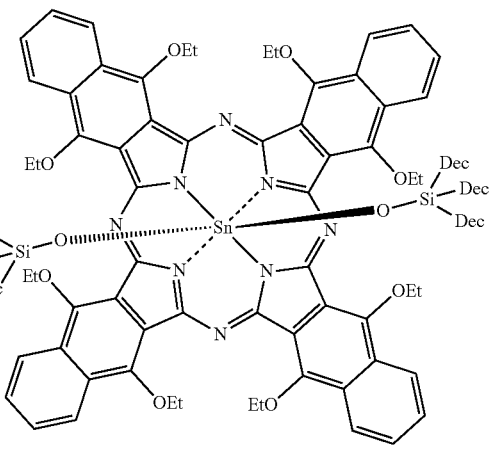

In a 1 L reaction vessel, 7.2 g of Si(C$_{10}$H$_{21}$)$_3$OH (10 eq) was dissolved in 343 mL of dehydrated xylene by stirring under an Ar atmosphere. Thereafter, 497 mg of sodium methoxide (6 eq) was added to the reaction vessel, followed by stirring at 160° C. for 1 hour.

To an obtained reaction liquid, 2.06 g of (OC$_2$H$_6$)$_8$SnBr$_2$Nc (1 eq) synthesized in Step (3) was added, followed by stirring at 160° C. overnight. After the completion of reaction was confirmed by TLC, the reaction liquid was cooled. Next, the reaction liquid was concentrated under vacuum and methanol wad added to obtained residue, whereby a solid was precipitated. The precipitated solid was filtered out, whereby 6.3 g of a crude product was obtained. The obtained crude product was purified with activated alumina and a concentrate of an obtained fraction was suspended and washed with methanol, followed by filtration. An obtained filter cake was vacuum-dried at 60° C., whereby 2.2 g of (OC$_2$H$_6$)$_8$Sn(OSi(C$_{10}$H$_{21}$)$_3$)$_2$Nc was obtained. The yield in this step was 69%.

An obtained compound was identified by $^1$H-NMR and MALDI-TOF-MS. Results are described below.

$^1$H-NMR (400 MHz, C$_6$D$_6$): δ (ppm)=9.13 (8H), 7.70 (8H), 5.65 (16H), 1.91 (24H), 1.31-0.4 (102H), −0.12 (12H), −1.12 (12H)

MALDI-TOF-MS measured value: m/z=2,120.30 [M$^-$]

The chemical formula of the target compound (OC$_2$H$_5$)$_8$Sn(OSi(C$_{10}$H$_{21}$)$_3$)$_2$Nc is C$_{124}$H$_{182}$N$_8$O$_{10}$Si$_2$Sn and the exact mass thereof is 2,119.75.

From the above results, it could be confirmed that the target compound was obtained by the above synthesis procedure.

Synthesis Example 2

Synthesis of (OC$_2$H$_6$)$_8$Sn(OSi(iC$_3$H$_7$)$_3$)$_2$Nc

A compound, (OC$_2$H$_5$)$_8$Sn(OSi(iC$_3$H$_7$)$_3$)$_2$Nc, represented by the following formula was synthesized in accordance with Steps (1) to (4) below:

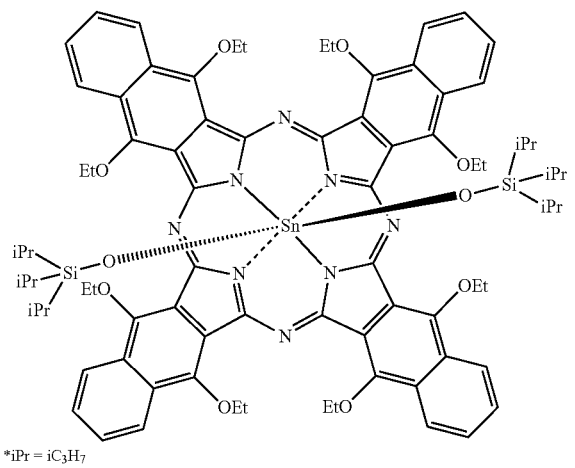

*iPr = iC$_3$H$_7$

Steps (1) to (3) through which (OC$_2$H$_5$)$_8$SnBr$_2$Nc was synthesized were performed in the same manner as that used in Example 1.

(4) Synthesis of (OC$_2$H$_5$)$_8$Sn(OSi(iC$_3$H$_7$)$_3$)$_2$Nc

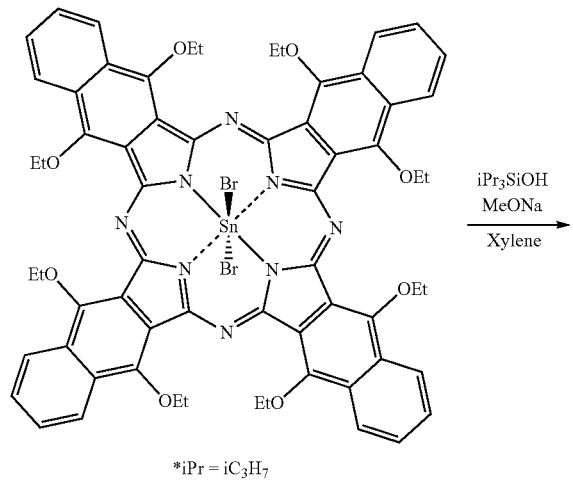

*iPr = iC$_3$H$_7$

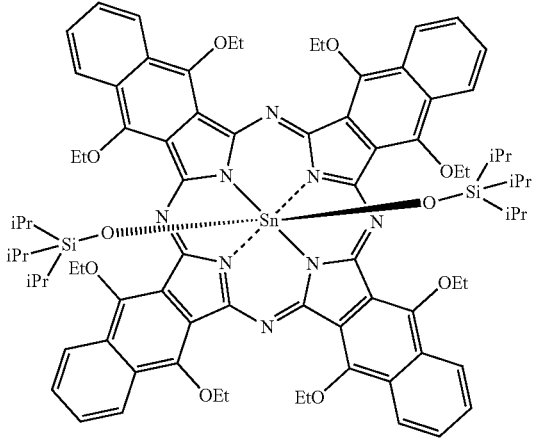

In a 1 L reaction vessel, 2.18 g of Si(iPr)$_3$OH (14.8 eq) was dissolved in 364 mL of dehydrated xylene by stirring under an Ar atmosphere. Thereafter, 719 mg of sodium methoxide (8.2 eq) was added to the reaction vessel, followed by stirring at 100° C. for 1 hour.

To an obtained reaction liquid, 2.18 g of (OC$_2$H$_5$)$_8$SnBr$_2$Nc (1 eq) synthesized in Step (3) was added, followed by stirring at 160° C. overnight. After the completion of reaction was confirmed by TLC, the reaction liquid was cooled. Next, the reaction liquid was concentrated under vacuum, followed by adding methanol to obtained residue, whereby a solid was precipitated. The precipitated solid was filtered out, whereby 2.14 g of a crude product was obtained. The obtained crude product was purified with activated alumina and a concentrate of an obtained fraction was suspended and washed with methanol, followed by filtration. An obtained filter cake was vacuum-dried at 60° C., whereby 1.0 g of (OC$_2$H$_5$)$_8$Sn(OSi(iC$_3$H$_7$)$_3$)$_2$Nc was obtained. The yield in this step was 40%.

An obtained compound was identified by $^1$H-NMR and MALDI-TOF-MS. Results are described below.

$^1$H-NMR (400 MHz, C$_6$D$_6$): δ (ppm)=9.09 (8H), 7.61 (8H), 5.61 (16H), 1.77 (24H), −0.37 (36H), −0.82 (6H)

MALDI-TOF-MS measured value: m/z=1,530.97 [M$^-$]

The chemical formula of the target compound (OC$_2$H$_5$)$_8$Sn(OSi(iC$_3$H$_7$)$_3$)$_2$Nc is C$_{82}$H$_{98}$N$_6$O$_{10}$Si$_2$Sn and the exact mass thereof is 1,530.60.

From the above results, it could be confirmed that the target compound was obtained by the above synthesis procedure.

A composition, photoelectric conversion element, and imaging device according to the present disclosure have been described above with reference to embodiments and examples. The present disclosure is not limited to these embodiments and examples. Those obtained by applying various modifications conceived by those skilled in the art to the above embodiments or examples and other embodiments structured by combining some components described in the above embodiments or examples without departing from the spirit of the present disclosure are also included in the scope of the present disclosure.

A composition and photoelectric conversion element according to the present disclosure may be applied to solar cells such that charges generated by light are extracted in the form of energy.

A composition according to the present disclosure may be applied to films, sheets, glasses, building materials, and the like in the form of a near-infrared light-blocking material or may be used in combination with ink, resin, glass, or the like in the form of an infrared absorber.

What is claimed is:

1. A composition containing a compound represented by the following formula:

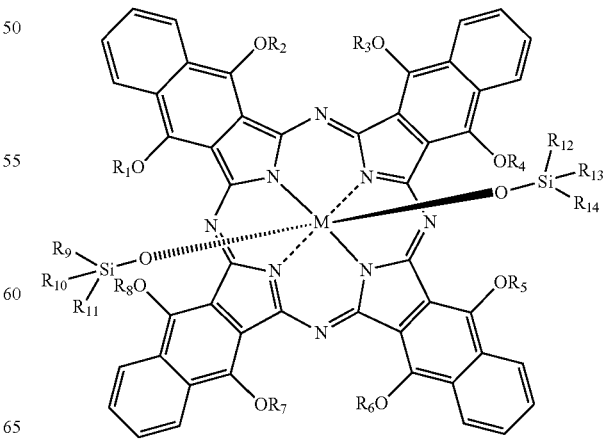

where M represents either of Si and Sn, $R_1$ to $R_8$ each independently represent an alkyl group containing three or less carbon atoms, and $R_9$ to $R_{14}$ each independently represent an alkyl group.

2. The composition according to claim 1, wherein in the formula, M is Sn.

3. The composition according to claim 1, wherein in the formula, $R_1$ to $R_8$ are ethyl groups.

4. The composition according to claim 1, wherein in the formula, $R_9$ to $R_{14}$ each independently represent an alkyl group containing 10 or less carbon atoms.

5. The composition according to claim 1, wherein in the formula, $R_9$ to $R_{14}$ are hexyl groups.

6. A photoelectric conversion element comprising:
   a first electrode;
   a second electrode; and
   a photoelectric conversion film which is disposed between the first electrode and the second electrode and which contains a compound represented by the following formula:

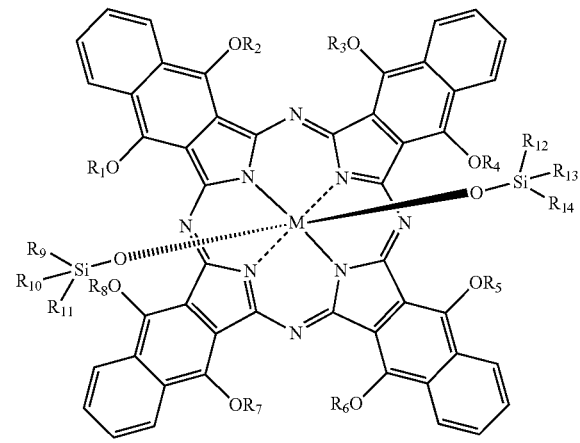

where M represents either of Si and Sn, $R_1$ to $R_8$ each independently represent an alkyl group containing three or less carbon atoms, and $R_9$ to $R_{14}$ each independently represent an alkyl group.

7. The photoelectric conversion element according to claim 6, wherein the photoelectric conversion film has a peak of absorption wavelength in a near-infrared region.

8. The photoelectric conversion element according to claim 7, wherein the position of the peak of the absorption wavelength is 900 nm or more.

9. An imaging device comprising:
   a substrate; and
   a unit pixel cell, wherein
   the unit pixel cell includes:
      a charge detection circuit provided in the substrate,
      a photoelectric converter disposed on the substrate, and
      a charge storage node electrically connected to the charge detection circuit and the photoelectric converter, and
   the photoelectric converter includes:
      a first electrode;
      a second electrode; and
      a photoelectric conversion film which is disposed between the first electrode and the second electrode and which contains a compound represented by the following formula:

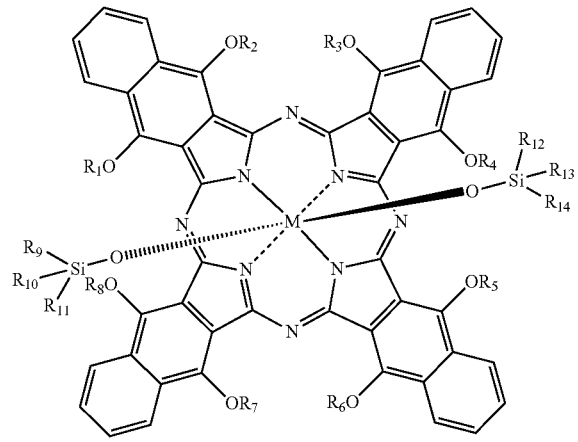

where M represents either of Si and Sn, $R_1$ to $R_8$ each independently represent an alkyl group containing three or less carbon atoms, and $R_9$ to $R_{14}$ each independently represent an alkyl group.

* * * * *